012) United States Patent
Yang et al.

(10) Patent No.: US 11,214,774 B2
(45) Date of Patent: Jan. 4, 2022

(54) PINK1 C-TERMINAL DOMAIN POLYPEPTIDE AND METHODS USING THE SAME IN CANCER TREATMENT

(71) Applicants: Andrew Man Chung Wo, Edgartown, MA (US); National Taiwan University, Taipei (TW); Academia Sinica, Taipei (TW)

(72) Inventors: Pan-Chyr Yang, Taipei (TW); Pei-Ying Lin, Taipei (TW); Bo-Tsang Huang, Taipei (TW)

(73) Assignees: Andrew Man Chung Wo, Edgartown, MA (US); National Taiwan University, Taipei (TW); Academia Sinica, Taipei (TW)

( * ) Notice: Subject to any disclaimer, the term of this patent is extended or adjusted under 35 U.S.C. 154(b) by 388 days.

(21) Appl. No.: 15/571,249

(22) PCT Filed: May 2, 2016

(86) PCT No.: PCT/US2016/030436
§ 371 (c)(1),
(2) Date: Nov. 1, 2017

(87) PCT Pub. No.: WO2016/179103
PCT Pub. Date: Nov. 10, 2016

(65) Prior Publication Data
US 2018/0112192 A1 Apr. 26, 2018

Related U.S. Application Data

(60) Provisional application No. 62/155,520, filed on May 1, 2015.

(51) Int. Cl.
| C07K 5/00 | (2006.01) |
| C12N 9/12 | (2006.01) |
| A61K 45/06 | (2006.01) |
| C07K 14/00 | (2006.01) |
| A61K 39/395 | (2006.01) |
| C07K 14/71 | (2006.01) |
| A61K 31/517 | (2006.01) |
| A61K 38/17 | (2006.01) |
| A61K 31/5377 | (2006.01) |
| A61P 35/00 | (2006.01) |
| A61K 38/45 | (2006.01) |

(52) U.S. Cl.
CPC .............. *C12N 9/12* (2013.01); *A61K 31/517* (2013.01); *A61K 31/5377* (2013.01); *A61K 38/179* (2013.01); *A61K 38/45* (2013.01); *A61K 39/395* (2013.01); *A61K 45/06* (2013.01); *A61P 35/00* (2018.01); *C07K 14/00* (2013.01); *C07K 14/71* (2013.01); *C12Y 207/11001* (2013.01); *C07K 2319/10* (2013.01); *C07K 2319/41* (2013.01); *C07K 2319/43* (2013.01)

(58) Field of Classification Search
None
See application file for complete search history.

(56) References Cited

U.S. PATENT DOCUMENTS

2012/0277286 A1* 11/2012 Youle ................. G01N 33/5079
514/44 A

OTHER PUBLICATIONS

NCBI, GenBank accession No. AAH09534.1 (Sep. 30, 2003) (Year: 2003).*

* cited by examiner

*Primary Examiner* — Meera Natarajan
(74) *Attorney, Agent, or Firm* — Mintz Levin Cohn Ferris Glovsky and Popeo, P.C.; Peter F. Corless; Joohee Lee

(57) ABSTRACT

The present disclosure includes a PINK1-C-terminal domain (PINK1-CTD) polypeptide that binds to ERBB tyrosine kinase domain (ERBB-TKD) and therefore impedes ERBB from dimerization and activation. The PINK1-CTD polypeptide inhibits, prevents and/or treats ERBB-expressing cancers. The disclosure demonstrates the anti-tumor function of the PINK1-CTD, which provides a new direction for ERBB-expressing cancer therapy.

7 Claims, 19 Drawing Sheets
Specification includes a Sequence Listing.

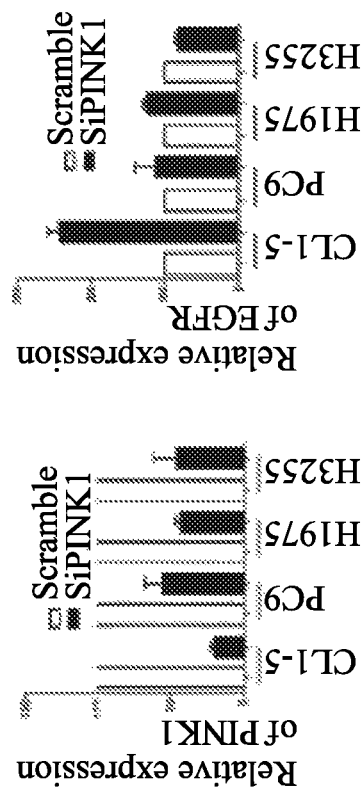
FIG. 2C
FIG. 2B
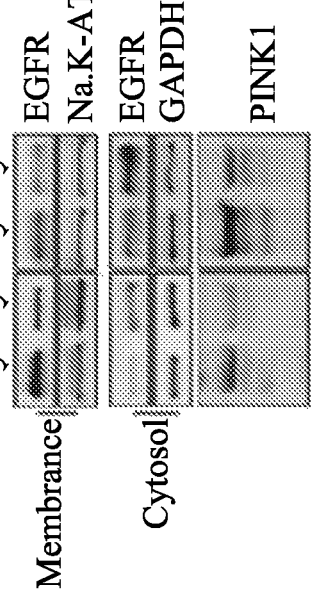
FIG. 2E
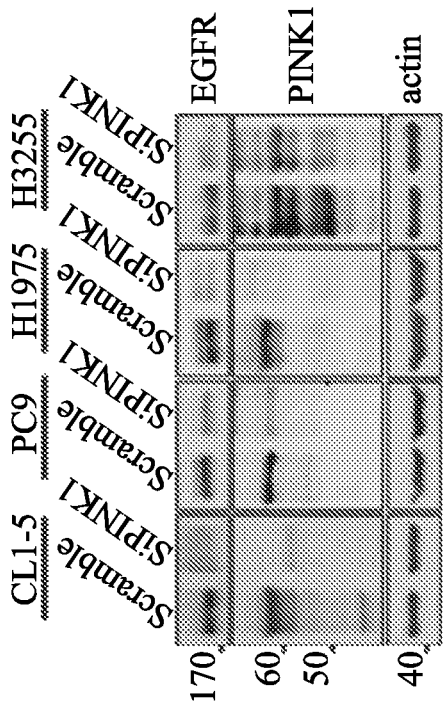
FIG. 2A
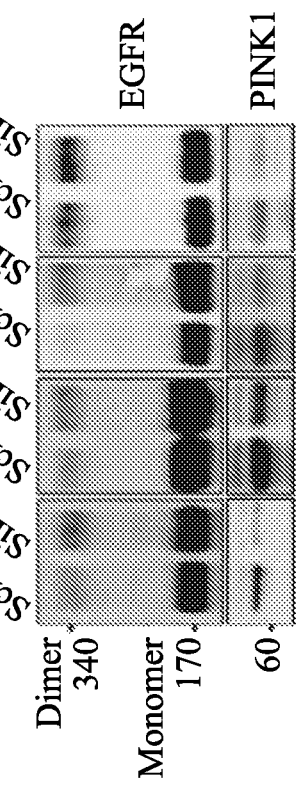
FIG. 2D

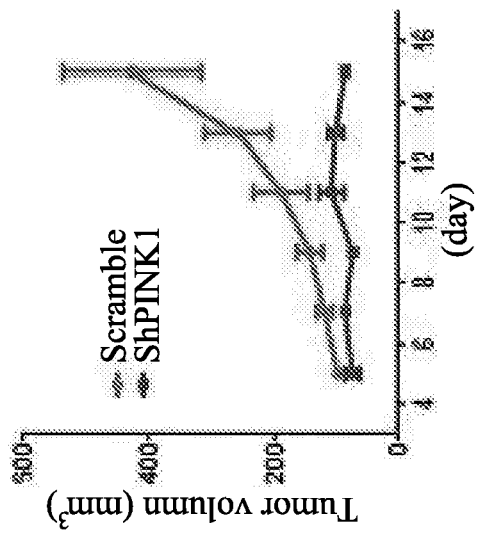
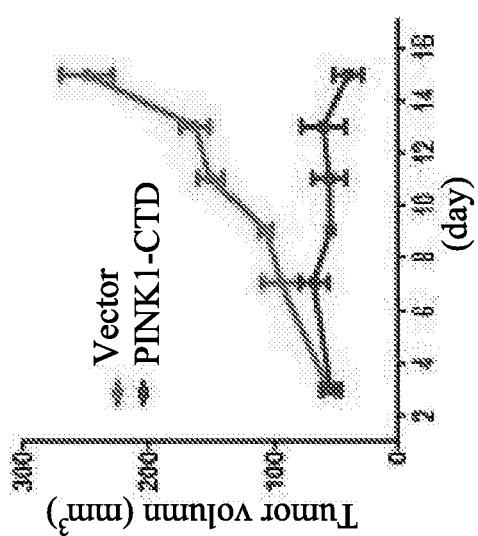
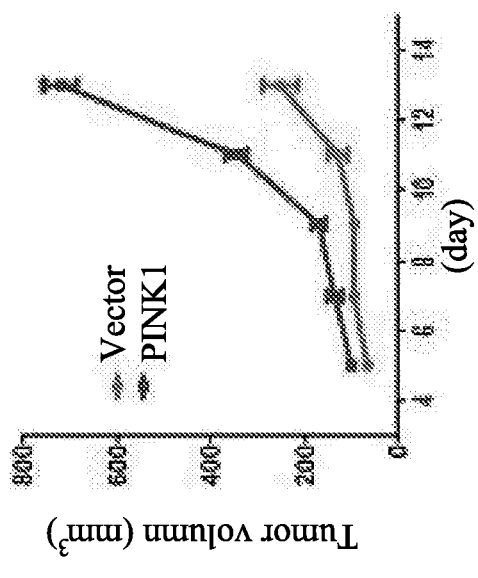
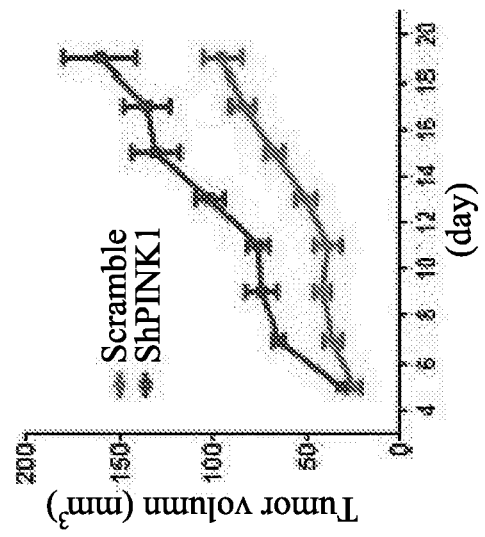
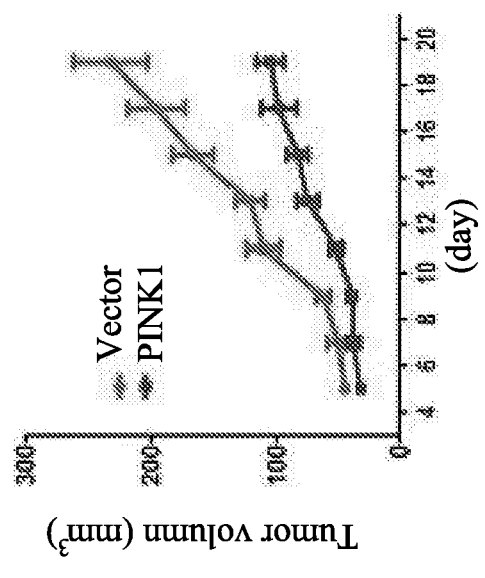
FIG. 6A  FIG. 6B  FIG. 6C
FIG. 6D  FIG. 6E  FIG. 6F

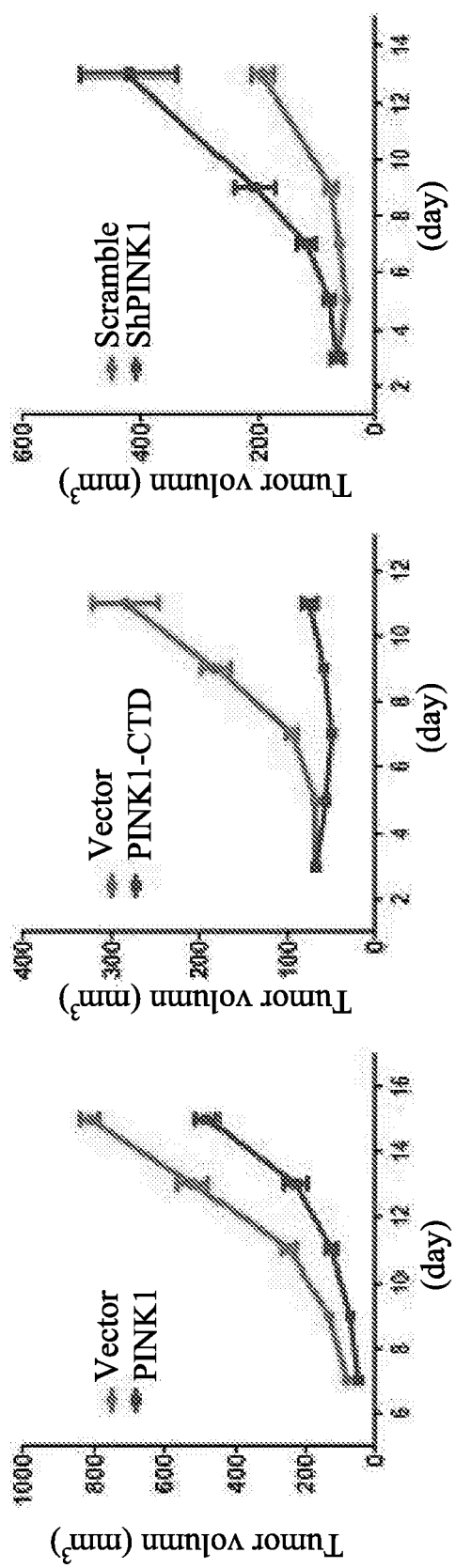
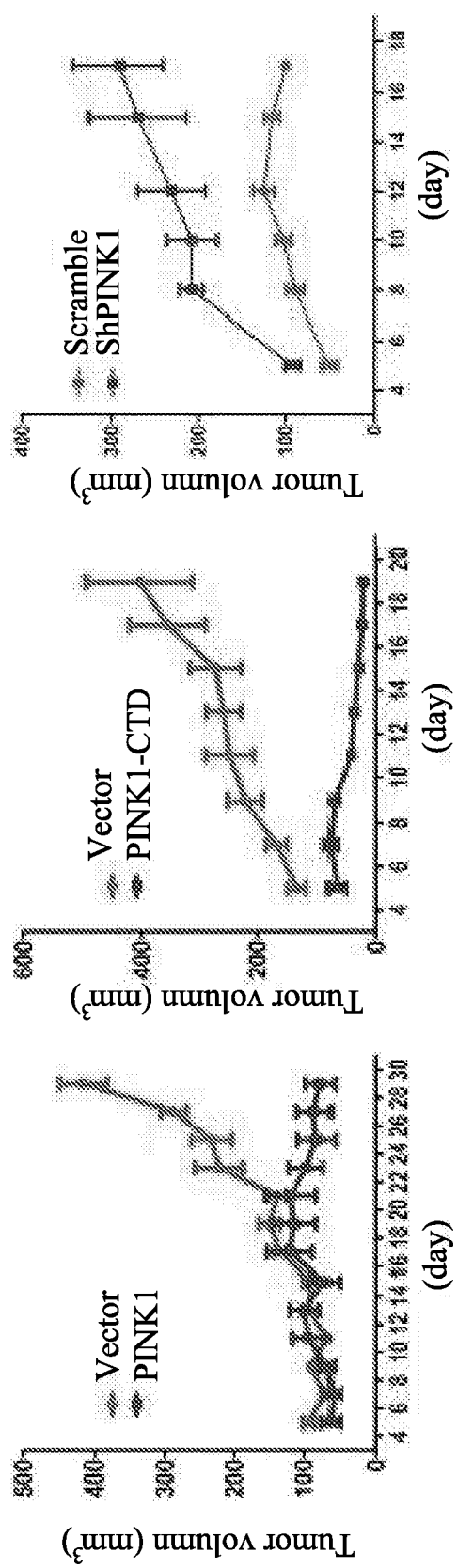
FIG. 6G  FIG. 6H  FIG. 6I
FIG. 6J  FIG. 6K  FIG. 6L

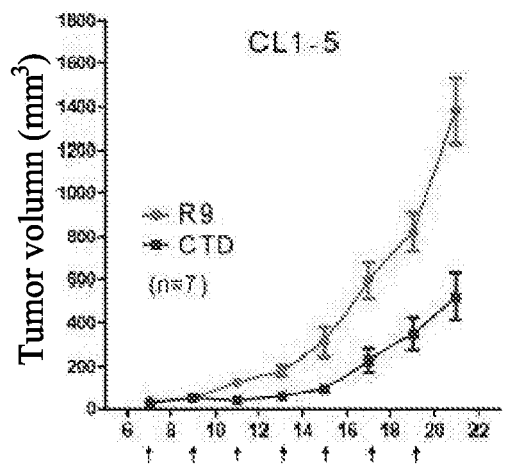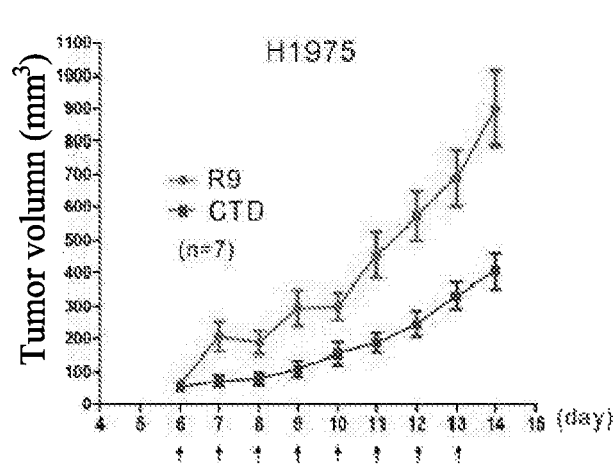
FIG. 11A    FIG. 11B
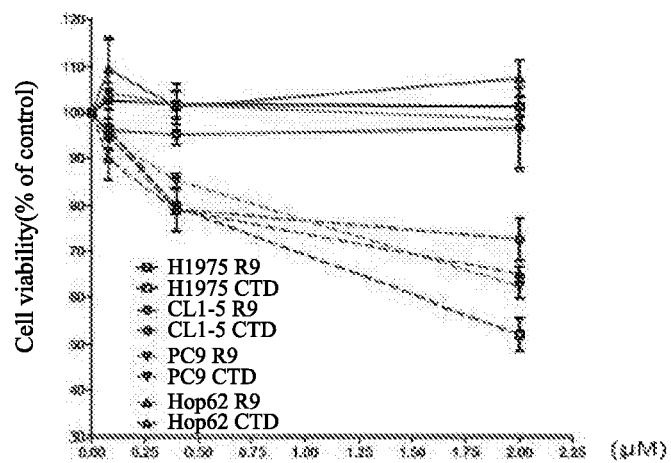
FIG. 11C

PINK1 C-TERMINAL DOMAIN POLYPEPTIDE AND METHODS USING THE SAME IN CANCER TREATMENT

CROSS REFERENCE TO RELATED APPLICATION

This application is a National Phase of PCT Application No. PCT/US2016/030436, file May 2, 2016 and claims priority to and the benefit of U.S. Provisional Application No. 62/155,520 filed May 1, 2016, the entire contents of which applications are incorporated by reference in its entirety.

TECHNICAL FIELD

The disclosure relates to a polypeptide for cancer treatment and a method of using the polypeptide to treat cancer. More particularly, the disclosure relates to PINK1 C-terminal domain (PINK1-CTD) in the treatment of ERBB-expressing cancers.

BACKGROUND

The identification of epidermal growth factor receptor (EGFR) tyrosine kinase domain (TKD) activating mutations in 2004 ushered in a new era for lung cancer therapy. Mutated EGFR functions as the driver gene in lung carcinogenesis in 50% of Asian and 10% of Caucasian lung adenocarcinomas. Unlike conventional ligand-dependent activation of wild-type EGFR, EGFR mutants are constitutively activated. Patients harboring activated EGFR mutants, most commonly exon 21 L858R substitutions (L858R) or exon 19 deletions (Ex19Del), usually present with good initial responses to EGFR tyrosine kinase inhibitors (EGFR-TKIs), but eventually develop disease progression after a median of 12 months. Acquired T790M mutation accounts for more than half of these resistant cases. In addition, de novo T790M is presented in approximately 25% of EGFR-TKI naïve lung adenocarcinoma cases and predicts short initial response duration to EGFR-TKIs. EGFR T790M, which produces a conformational change in the ATP-binding pocket that increases receptor affinity for its natural substrate ATP, remains an unsolved problem in lung adenocarcinoma management (C. H. Yun et al. *Proc. Natl. Acad. Sci. U.S.A* 105, 2070-2075 (2008)).

PTEN-induced putative kinase 1 (PINK1) was identified in 2001 as a potential tumor suppressor owing to its upregulation by PTEN in cancer cells (M. Unoki, Y. Nakamura. *Oncogene*. 22, 2172-2185 (2003)). Fruitful study on PINK1 began at the point when its role in hereditary early-onset Parkinson's disease was reported. PINK1 encodes a 581-amino-acid protein with a mitochondrial-targeting sequence, a conserved serine/threonine kinase domain, and a C-terminal domain. It is a major regulator of mitochondrial quality control and possesses cytoprotective and anti-apoptotic functions through the PI3K-AKT-mTOR axis or autophagic pathways (H. Murata et al. *J. Biol. Chem.* 286, 7182-7189 (2011); G. Arena et al. *Cell. Death. Differ.* 20, 920-930 (2013)).

Reports on the role of PINK1 in cancer biology are somewhat contradictory. Direct evidence supporting its tumor suppressive role is lacking. Although PINK1 gene is located on chromosome 1p36, a region postulated to contain tumor-suppressive activity, and is associated with tumor suppressors, PTEN, FOXO3a, Beclin-1 and Parkin, its anti-proliferation effect cannot be proved (Y. Mei et al. *Proc. Natl. Acad. Sci. U.S.A* 106, 5153-5158 (2009); Y. Gong et al. *Nat. Genet.* 46, 588-594 (2014)). On the other hand, quite a few studies suggest an oncogenic role for PINK1. High-throughput RNA interference screenings show the relationship between PINK1 knockdown and Taxol sensitivity and identify PINK1 as a therapeutic target for malignancies with DNA mismatch repair deficiencies (S. A. Martin, M. Hewish, D. Sims, C. J. Lord, A. Ashworth. *Cancer. Res.* 71, 1836-1848 (2011)). Moreover, PINK1 has been found to be necessary for optimal activation of IGF-1-dependent AKT signaling, to enhance AKT-S473 phosphorylation via mTORC2, and to regulate cell cycle progression in cancer cells. Studies show that PINK1 functions in anti-apoptosis, cell motility promotion and cell cycle regulation in cancer cells (H. Murata et al. *J. Biol. Chem.* 286, 7182-7189 (2011); R. S. Akundi, L. Zhi, H. Büeler. *Neurobiol. Dis.* 45, 469-478 (2012); C. H. O'Flanagan, V. A. Morais, W. Wurst, B. De Strooper, C. O'Neill. *Oncogene*. (2014)).

Accumulating evidence supports the involvement of PINK1 in cancer biology but its exact role remains puzzling. EGFR has been the most-studied receptor tyrosine kinase over the past decade but its activation mechanism is still not fully understood. The identification of EGFR mutations and the development of EGFR-TKIs are cutting edge breakthroughs in lung cancer therapy but drug-resistance remains an unsolved problem. It is worthy to develop a new agent to treat EGFR-expressing cancers by exploring the interplay between PINK1 and EGFR.

SUMMARY

In one aspect, the disclosure provides a non-natural polypeptide binding to ERBB tyrosine kinase domain (ERBB-TKD). In one embodiment, the disclosure provides a non-natural polypeptide comprising an amino acid sequence having at least 10% identity to SEQ ID NO:1 or a biologically active variant thereof, wherein the polypeptide binds to ERBB-TKD, with the proviso that an amino acid sequence identical to SEQ ID No:2 is excluded. In another embodiment, the disclosure provides a non-natural polypeptide comprising a fragment having from about 3 to about 72 consecutive amino acid residues of SEQ ID NO:1 or a biologically active variant thereof, wherein the polypeptide binds to ERBB-TKD.

In another aspect, the disclosure provides a pharmaceutical composition comprising a therapeutically effective amount of the polypeptide of the disclosure, and a pharmaceutically acceptable carrier. In one embodiment, the pharmaceutically acceptable carrier is a micelle, a liposome, or the like.

In one aspect, the present disclosure provides a method for impeding EGFR from dimerization and activation, comprising administering a therapeutically effective amount of the PINK1-CTD polypeptide of the disclosure to a subject in need thereof. In one embodiment, the disclosure provides a method for inhibition, prevention and/or treatment of a cancer (preferably an ERBB-expressing cancer), comprising administering a therapeutically effective amount of the non-natural polypeptide of the disclosure to a subject. Preferably, the cancer is a lung cancer; more preferably, the lung cancer is lung adenocarcinoma.

BRIEF DESCRIPTION OF THE DRAWING

FIG. 1A: Immunoblotting of endogenous EGFR-pY1068, EGFR and PINK1 in CL1-5, PC9, H1975 and H3255 cells; FIG. 1B: Immunoprecipitation revealed an interaction between endogenous PINK1 and EGFR; and FIG. 1C: Wild-type EGFR-GFP (green) and PINK1-myc (red) were co-overexpressed in CL1-5 cells. Confocal images demonstrated the co-localization of EGFR and PINK1 (yellowish) (I and II). 3D-structured illumination microscopy images specifically disclosed the interaction beneath the cytoplasmic membrane (III and IV).

FIGS. 2A-2E show inhibition of EGFR dimerization and internalization by PINK1. FIG. 2A: Immunoblotting demonstrated a decrease in total EGFR along with PINK1 knockdown in CL1-5, PC9, H1975 and H3255 cells; FIGS. 2B and 2C: RT-qPCR revealed no decrease in EGFR mRNA despite sufficient decrease in PINK1 mRNAs; FIG. 2D: EGFR dimerization assays demonstrated an increase in EGFR dimer to monomer ratio under PINK1 knockdown when EGFR monomers were normalized to equal in each control and knock-down groups; and FIG. 2E: The membranous fraction of EGFR protein was decreased and the cytoplasmic fraction of EGFR protein was increased under PINK1 knockdown, indicating an increase in receptor internalization.

FIG. 3A: Schematic representation of 9 flag-fused EGFR constructs, containing amino acids 1-1210, 1-378, 1-621, 1-644, 1-690, 1-954, 645-1210, 645-954, and 955-1210; FIG. 3B: Immunoprecipitation results showed that only construct E, F, G and I (star in A) that contained the tyrosine kinase domain interacted with PINK1; FIG. 3C: Schematic representation of 8 myc-fused PINK1 constructs, containing amino acids 1-581, 1-509, 1-155, 156-509, 156-309, 310-428, 429-581 and 78-581; FIG. 3D: Immunoprecipitation results showed that only construct A, G and H (star in C) that contained the C-terminal domain interacted with EGFR; FIG. 3E: In vitro GST pull-down assay demonstrated the direct interaction between PINK1-CTD and EGFR-TKD. MTS: mitochondria targeting sequence. TM: transmembrane domain.

FIG. 5A: 2 µM CTD polypeptide effectively inhibited EGFR phosphorylation in CL1-5, HOP62, PC9 and H1975; FIG. 5B: CTD treatment showed dose-dependent inhibition of HER2 phosphorylation in CL1-5 cell; FIG. 5C: Amino acid sequence alignment of the tyrosine kinase domain of ERBB1 to ERBB4 (HER1 to HER4) revealed high sequence homology. R9: a peptide consisting of 9 arginine residues.

FIGS. 6A-6L show tumor xenografts of shPINK1, PINK1 and PINK1-CTD stably expressing lung cancer cells. FIGs. A, D, G and J: PINK1 overexpression aggravated tumor growth in CL1-5 cells but suppressed tumor growth in PC9, H1975 and H3255 cells; FIGs. B, E, H and K: PINK1-CTD overexpression inhibited tumor growth in all cells tested; FIGs. C, F, I and L: PINK1 knockdown inhibited tumor growth in CL1-5 cells but promoted tumor growth in PC9, H1975 and H3255 cells. N=7 in each group.

FIG. 7A: Immunoblotting demonstrated an increase in total EGFR along with PINK1 overexpression in CL1-5, PC9, H1975 and H3255 cells; FIG. 7B: RT-qPCR analyses of EGFR mRNA revealed no obvious alteration when PINK1 was overexpressed; and FIG. 7C: The EGFR dimerization assays of CL1-5, PC9, H1975 and H3255 cells demonstrated a decrease in EGFR dimer to monomer ratio under PINK1 overexpression when EGFR monomers were normalized to equal in each control and overexpression groups.

FIG. 9A: EGFR dimerization assays of CL1-5, PC9, H1975 and H3255 cells demonstrated a decrease in EGFR dimer to monomer ratio under PINK1-CTD overexpression when EGFR monomers were normalized to equal in each control and overexpression group; and FIG. 9B: Immunoblotting results showed a decrease in phosphorylated EGFR-Y1068 to total EGFR ratio in all cells analyzed. EGFR downstream signaling was concurrently downregulated under PINK1-CTD overexpression in EGFR-addicted PC9, H1975 and H3255 cells. When EGFR-Y1068 phosphorylation was attenuated by PINK1-CTD in wild-type EGFR CL1-5 cells, there was only a decrease in STAT3-Y705 phosphorylation.

FIGS. 11A-11C show that CTD treatment inhibits tumor growth. FIGS. 11A and 11B: CTD treatment inhibited in vivo tumor growth in CL1-5 and H1975 lung cancer mouse xenograft models. FIG. 11C: CTD treatment reduced cancer cell viability as demonstrated by the in vitro MTT assay. R9: a peptide consisting of 9 arginine residues.

DETAILED DESCRIPTION

Figure 1A:
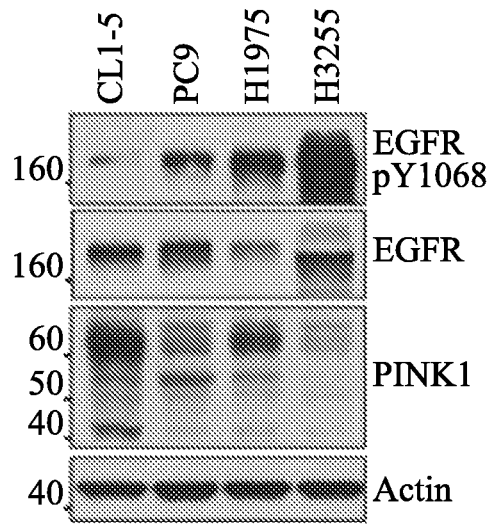
FIGS. 1A-1C show interaction between PINK1 and EGFR in lung adenocarcinoma cells.

The identification of EGFR mutations and the development of EGFR-TKIs are cutting edge breakthroughs in lung cancer therapy but drug-resistance remains an unsolved problem. The disclosure is based on at least the interplay between ERBB and PINK1 and dissects the role of PINK1 in ERBB-expressing cancers. The disclosure demonstrates the anti-tumor function of the PINK1 C-terminal domain (PINK1-CTD), which may provide a new direction for ERBB-expressing cancer therapy.

Definitions

Before the present nucleotides, polypeptides, compositions, articles, devices, and/or methods are disclosed and described, it is to be understood that this disclosure is not limited to specific synthetic methods, specific treatment regimens, or to particular purification procedures, as such may, of course, vary. It is also to be understood that the terminology used herein is for the purpose of describing particular embodiments only and is not intended to be limiting.

As used herein, the singular forms "a," "an" and "the" include plural referents unless the context clearly dictates otherwise. Thus, for example, reference to "a polypeptide" includes mixtures of polypeptides, reference to "a pharmaceutical carrier" includes mixtures of two or more such carriers, and the like.

As used herein, the term "polypeptide" is a polymer of amino acid residues preferably joined exclusively by peptide bonds, whether produced naturally or synthetically. A polypeptide produced by expression of a non-host DNA molecule is a "heterologous" peptide or polypeptide. An "amino acid residue" can be a natural or non-natural amino acid residue linked peptide bonds or bonds different from peptide bonds. The amino acid residues can be in D-configuration or L-configuration.

As used herein, the term "isolated polypeptide" or "purified polypeptide" is a polypeptide that is essentially free from contaminating cellular components, such as carbohydrate, lipid, or other polypeptideaceous impurities associated with the polypeptide in nature. Typically, a preparation of isolated polypeptide contains the polypeptide in a highly purified form. One way to show that a particular polypeptide preparation contains an isolated polypeptide is by the appearance of a single band following sodium dodecyl sulfate (SDS)-polyacrylamide gel electrophoresis of the polypeptide preparation and Coomassie Brilliant Blue staining of the gel. However, the term "isolated" does not exclude the presence of the same polypeptide in alternative physical forms, such as dimers or alternatively glycosylated or derivatized forms.

As used herein, the terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "sequence identity" or, for example, comprising a "sequence 10% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 10%, 20%, 30%, 40%, 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

As used herein, the term "expression" refers to the biosynthesis of a gene product. For example, in the case of a structural gene, expression involves transcription of the structural gene into mRNA and the translation of mRNA into one or more polypeptides.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

As used herein, the terms "subject" or "patient" are used interchangeably to refer to an animal. In a specific embodiment, a subject is a mammal. In another embodiment, a subject is a human.

As used herein, the terms "therapies" and "therapy" can refer to any protocol(s), method(s), composition(s), formulation(s), and/or agent(s) that can be used in the prevention or treatment of a cancer or a disease or symptom associated therewith. In certain embodiments, the terms "therapies" and "therapy" refer to biological therapy, supportive therapy, and/or other therapies useful in treatment or prevention of cancer or a disease or symptom associated therewith known to one of skill in the art.

As used herein, the term "therapeutically effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy.

As used herein, the term "in combination" in the context of the administration of a therapy to a subject refers to the use of more than one therapy (e.g., prophylactic and/or therapeutic). The use of the term "in combination" does not restrict the order in which the therapies, concomitantly with, or subsequent to the administration of a second therapy to a subject which had, has, or is susceptible to a cancer. In some embodiment, the therapies are administered to a subject in a sequence and within a time interval such that the therapies can act together. In an embodiment, the therapies are administered to a subject in a sequence and within a time interval such that they provide an increased benefit than if they were administered otherwise. Any additional therapy can be administered in any order with the other additional therapy.

As used herein, the terms "prevent," "preventing" and "prevention" in the context of the administration of a therapy to a subject refer to the prevention or inhibition of the recurrence, onset, and/or development of brain cancer or a symptom thereof in a subject resulting from the administration of a therapy (e.g., a prophylactic or therapeutic agent), or a combination of therapies (e.g., a combination of prophylactic or therapeutic agents).

As used herein, the PTEN-induced putative kinase 1 (PINK1) is a mitochondrial serine/threonine-protein kinase encoded by the PINK1 gene. PINK1 activity causes the parkin protein to bind to depolarized mitochondria to induce autophagy of those mitochondria.

As used herein, the erythroblastic leukemia viral oncogene homolog (ERRB) includes four members, EGFR (EGF Receptor)/ErbB1/Her1 (Heregulin-1), ErbB2/Her2 (Heregulin-2), ErbB3/Her3 (Heregulin-3), and ErbB4/Her4 (Heregulin-4). ErbB overexpression is associated with tumorigenesis of the breast, prostate, ovary, liver, bladder, esophagus, larynx, stomach, colon, and lung.

As used herein, the epidermal growth factor receptor (EGFR; also known as ErbB-1 and HER1 in humans) is the cell-surface receptor for members of the epidermal growth factor family (EGF-family) of extracellular protein ligands.

As used herein, the term "mutant" or "mutation" refers to a molecule (e.g., a polypeptide or a polynucleotide) that has a different structure than the wild-type molecule. That difference in structure from the wild-type molecule includes, without limitation, a different sequence (e.g., a different amino acid or nucleotide sequence), additional sequences, missing sequences (i.e., a portion of the sequence is missing), changes in modification (methylation, phosphorylation, etc.), and/or fusion of all or part of the wild-type molecule with another molecule. The term "wild-type" refers to a gene or gene product (e.g., a polypeptide) that has the characteristics of that gene or gene product when isolated from a naturally-occurring source. A wild type gene or gene product is that which is most frequently observed in a population and is thus arbitrarily designed the "normal" or "wild-type" form of the gene.

PINK1 C-Terminal Domain (PINK1-CTD) Polypeptides

The present disclosure encompasses PINK1-CTD polypeptides that bind to ERBB tyrosine kinase domain (ERBB-TKD) and therefore impede EGFR from activation. The PINK1-CTD polypeptide functions to inhibit, prevent and/or treat ERBB-expressing cancers. Particularly, the PINK1-CTD polypeptide alone can directly inhibit EGFR activation in both wild-type and mutant EGFR cells and suppress tumor growth. The disclosure discloses that PINK1 physically associates with HER1 and suppresses its signaling and suggests the therapeutic potential of PINK1-CTD in ERBB-expressing cancer therapy.

In one aspect, the disclosure provides a polypeptide binding to ERBB tyrosine kinase domain (ERBB-TKD).

In one embodiment, the disclosure provides a polypeptide comprising an amino acid sequence having at least 10% identity to an amino acid sequence of SEQ ID NO:1 or a biologically active variant thereof, wherein the polypeptide binds to EGFR-TKD. In a further embodiment, the disclosure provides a polypeptide comprising at least 10%, 20%, 30%, 40%, 50%, 55%, 60%, 65%, 70%, 75%, 80%, 85%, 90%, 95%, 96%, 97%, 98% or 99% sequence identity to the amino acid sequence of SEQ ID NO:1 or a biologically active variant thereof.

In one embodiment, the disclosure provides a polypeptide comprising a modified amino acid sequence of SEQ ID NO:1 having one or more substitution, deletion, addition and/or insertion, wherein the polypeptide binds to ERBB-TKD.

In one embodiment, the disclosure provides a polypeptide comprising a fragment having from about 3 to about 72 consecutive amino acid residues of SEQ ID NO:1 or a biologically active variant thereof, wherein the polypeptide binds to ERBB-TKD. In one embodiment, the ERBB-TKD is EGFR-TKD. In some embodiments, the polypeptide is a polymer of 3 to 10, 10 to 15, 10 to 20, 10 to 25, 10 to 30, 10 to 40, 10 to 50, or 10 to 60, 10 to 70 amino acids linked by covalent amide bonds. In some embodiment, the polypeptide comprises from about 3 to about 70, about 3 to about 60, about 3 to about 50, about 3 to about 40, about 3 to about 30, about 3 to about 20, about 10 to about 70, about 10 to about 60, about 10 to about 50, about 10 to about 40, about 10 to about 30 or about 10 to about 20, about 10 to about 15 amino acid residues. A polypeptide can be a polymer of 8, 9, 10, 15, 20, 25, 30, 35, 40, 45, 50, 55, 60, 65, 70, 71, 72, or more amino acids linked by covalent amide bonds.

In one embodiment, the disclosure provides a polypeptide further comprising one or more additional amino acid sequences. In one embodiment, the additional amino acid sequence may be a peptide or protein tag sequence, a targeting sequence, a penetrating peptide sequence (e.g., a cell-penetrating sequence), or a linking sequence (e.g., a sequence degradable by a proteinase such as an endoproteinase). In a further embodiment, the peptide or protein tag may be polyhistidine-tag. In some embodiments, the penetrating peptide sequence may comprise 9 arginine residues for membrane attaching and internalization.

The amino acid sequence of SEQ ID NO: 1 is as follows:

```
                                              (SEQ ID NO: 1)
SLWGEHILALK NLKLDKMVGW LLQQSAATLL ANRLTEKCCV

ETKMKMLFLA NLECETLCQA ALLLCSWRAA L
```

The PINK-CTD polypeptide of the disclosure locates in the PINK1 C-terminal domain from amino acids 510 to 581 of PINK1. The sequence of PINK1 is as follows:

```
                                              (SEQ ID NO: 2)
         10          20          30          40
  MAVRQALGRG  LQLGRALLLR  FTGKPGRAYG  LGRPGPAAGC 50          60          70          80
  VRGERPGWAA  GPGAEPRRVG  LGLPNRLRFF  RQSVAGLAAR 90         100         110         120
  LQRQFVVRAW  GCAGPCGRAV  FLAFGLGLGL  IEEKQAESRR 130         140         150         160
  AVSACQEIQA  IFTQKSKPGP  DPLDTRRLQG  FRLEEYLIGQ 170         180         190         200
  SIGKGCSAAV  YEATMPTLPQ  NLEVTKSTGL  LPGRGPGTSA 210         220         230         240
  PGEGQERAPG  APAFPLAIKM  MWNISAGSSS  EAILNTMSQE 250         260         270         280
  LVPASRVALA  GEYGAVTYRK  SKRGPKQLAP  HPNIIRVLRA 290         300         310         320
  FTSSVPLLPG  ALVDYPDVLP  SRLHPEGLGH  GRTLFLVMKN 330         340         350         360
  YPCTLRQYLC  VNTPSPRLAA  MMLLQLLEGV  DHLVQQGIAH 370         380         390         400
  RDLKSDNILV  ELDPDGCPWL  VIADFGCCLA  DESIGLQLPF 410         420         430         440
  SSWYVDRGGN  GCLMAPEVST  ARPGPRAVID  YSKADAWAVG 450         460         470         480
  AIAYEIFGLV  NPFYGQGKAH  LESRSYQEAQ  LPALPESVPP 490         500         510         520
  DVRQLVRALL  QREASKRPSA  RVAANVLHLS  LWGEHILALK 530         540         550         560
  NLKLDKMVGW  LLQQSAATLL  ANRLTEKCCV  ETKMKMLFLA 570         580
  NLECETLCQA  ALLLCSWRAA  L
```

Standard recombinant DNA techniques may be used to prepare the polypeptides of the disclosure. Within one embodiment, DNA encoding the PINK1-CTD fragment may be obtained by polymerase chain reaction (PCR) amplification of the PINK1 fragment sequence (see, PCR Technology: Principles and Applications for DNA Amplification, Erlich (ed.), Stockton Press (1989)). The amplified PINK1-

CTD fragment DNA may then be readily inserted into an expression vector. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. The PINK1-CTD isolated polypeptides of the present disclosure may be produced by expressing the encoding nucleic acid in host cells. The nucleic acid may be transformed or transfected into host cells. Accordingly, some aspects of the present disclosure include the transformation and/or transfection of nucleic acid encoding the PINK1-CTD isolated polypeptides. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

Another means of preparing a nucleic acid molecule encoding the amino acid sequence of a polypeptide is chemical synthesis using methods well known to the skilled artisan such as those described by Engels et al., 1989, Angew. Chem. Intl. Ed. 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Other methods known to the skilled artisan may be used as well.

According to the disclosure, PINK1-CTD polypeptide of the disclosure alone can directly inhibit EGFR activation in both wild-type and mutant EGFR cells and suppress in vivo tumor growth, whereby suggesting the therapeutic potential of PINK1-CTD in cancer therapy.

Activating mutations in the EGFR converts it into a driver oncogene in EGFR-expressing cancers. An "EGFR mutant" includes any type of mutation (i.e., change) in an EGFR molecule that renders the EGFR mutant different than wild-type EGFR. In some embodiments, the mutation increases the kinase activity of the EGFR molecule and/or renders a tumor cell sensitive to one or more EGFR inhibitors. In some embodiments, the mutation is in the kinase domain of EGFR. In some embodiments, the mutation is in one of exons 18 to 21 of the human EGFR gene. The most common EGFR mutations are deletions within exon 19 (e.g., a 15-bp nucleotide in-frame deletion in exon 19 (Del E746-A750) and a point mutation replacing leucine with arginine at codon 858 in exon 21 (L858R). The ability to detect mutated gene products in cancer cells can identify patients most likely benefit from such therapies, and make clinical trials more efficient and informative.

EGFR mutants can be detected by standard means known in the art. For example, mutants can be detected at the nucleotide level by sequencing, nucleic acid amplification using primers and/or probes specific for the wild-type or mutant sequence, and amplification and length analysis to detect deletional mutants. Exemplary methods to determine EGFR mutational status are disclosed in Rosell et al., 2009, N. Engl. J. Med., 361:958-967 and Li et al., 2011, PLoS ONE, 6: e28204. Kits for nucleic acid analysis are commercially available, e.g., EGFR Pyro Kit (QIAGEN), EGFR PCR Kit (QIAGEN), and EGFR RGQ PCR Kit (QIAGEN). The EGFR RGQ PCR Kit is capable of detecting 29 mutations in the EGFR gene, including 19 deletions in exon 19, T790M, L858R, L861A, S768I, and G719X (detects the presence of G719S, G719A, or G719C but does not distinguish among them).

Specific EGFR mutants can be detected at the polypeptide level (e.g., by western blot or immunohistochemistry) using mutant-specific antibodies, e.g., EGF Receptor (E746-A750del Specific) (6B6) XP® Rabbit mAb or EGF Receptor (L858R Mutant Specific) (43B2) Rabbit mAb, both from Cell Signaling Technology, Inc. (Danvers, Mass.) or mutation-specific AQUA peptides (Stemmann et al., 2001, Cell, 107: 715-726). Mutant-specific antibodies can be prepared that bind specifically to other identified mutant EGFR polypeptides.

Administration and Pharmaceutical Compositions

In another aspect, the present disclosure provides a pharmaceutical composition comprising a therapeutically effective amount of the PINK1-CTD isolated polypeptide of the disclosure. In one embodiment, the pharmaceutical composition of the disclosure is a suppressor that inhibits HER from activation through physical association. In one embodiment, the pharmaceutical composition of the disclosure further comprises an additional anti-cancer agent. Preferably, the additional anti-cancer agent is an EGFR inhibitor. Various EGFR inhibitors are known and can be used in the methods disclosed herein, including gefitinib, erlotinib, cetuximab, afatinib, necitumumab, nimotuzumab, PF299804 (Janne et al., 2011, Clin. Cancer Res., 17:1131-39), RO5083945 (glycoengineered anti-EGFR monoclonal antibody; Hoffmann-La Roche; Markman et al., 2010, J. Clin. Oncol., 28:15s, abstr 2522), ABT-806 (humanized anti-EGFR monoclonal antibody; Abbott), NVP-TAE684 (Katayama et al., 2011, Proc. Natl. Acad. Sci. USA, 108: 7535-40), and AP26113.

In one aspect, the present disclosure provides a method for impeding EGFR from dimerization and activation, comprising administering a therapeutically effective amount of the PINK1-CTD isolated polypeptide of the disclosure to a subject. In one embodiment, the disclosure provides a method for inhibition, prevention and/or treatment of a cancer, comprising administering a therapeutically effective amount of the PINK1-CTD isolated polypeptide of the disclosure to a subject. In one embodiment, the cancer is an ERBB-expressing cancer, such as breast cancer, prostate cancer, ovarian cancer, liver cancer, bladder cancer, esophageal cancer, laryngeal cancer, gastric cancer, colon cancer, and lung cancer; more preferably, a lung cancer; more preferably, the lung cancer is lung adenocarcinoma. In some embodiments, the lung cancer is small cell lung cancer (SCLC) or non-small cell lung cancer (NSCLC).

The pharmaceutical composition may further comprise pharmaceutically acceptable carriers, excipients, or stabilizers known in the art (see generally Remington, (2005) The Science and Practice of Pharmacy, Lippincott, Williams and Wilkins). The formulation is made to suit the mode of administration. In general, methods of administering proteins are known to those of ordinary skill in the art and can be applied to administration of the polypeptides of the disclosure.

Administration is by any of the routes normally used for introducing a molecule into ultimate contact with blood or tissue cells. Suitable methods of administering such polypeptides in the context of the present disclosure to a subject are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure.

The PINK1-CTD isolated polypeptide of the disclosure may be administered by any conventional route suitable for proteins or peptides, including, but not limited to, those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intrathecal, intraarterial, or intravenous), topical (i.e., both skin and mucosal surfaces, including airway surfaces), pulmonary, intraocular, intranasal, and transdermal administration, although the most suitable route in any given case will depend on the nature and severity of the condition being treated. Administration can be either local or systemic. The PINK1-CTD isolated polypeptide of the disclosure may be used in combination with other agents or therapeutics.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of PINK1-CTD isolated polypeptide of the disclosure can be presented in unit-dose or multi-dose sealed containers, such as ampules and vials.

The dose administered to a subject, in the context of the present disclosure, is sufficient to have a beneficial therapeutic response in the patient over time, or other appropriate activity, depending on the application. The dose is determined by the efficacy of the particular PINK1-CTD isolated polypeptide of the disclosure, or formulation, and the activity of the polypeptide employed and the condition of the subject, as well as the body weight or surface area of the subject to be treated. The size of the dose is also determined by the existence, nature, and extent of any adverse side-effects that accompany the administration of a particular vector, formulation, or the like in a particular subject.

The dose administered is typically in the range equivalent to dosages of currently-used therapeutic proteins, adjusted for the altered activity or serum half-life of the relevant composition. The PINK1-CTD isolated polypeptides of the disclosure or pharmaceutical formulations of this disclosure can supplement treatment conditions by any known conventional therapy, including radiotherapy, chemotherapy, immunotherapy, antibody administration, vaccine administration, administration of cytotoxic agents, and the like. For example, the chemotherapy comprises administering an additional anti-cancer agent to a subject.

EXAMPLE

Example 1 Interaction Between PINK1 and EGFR in Lung Adenocarcinoma

Figure 1B:
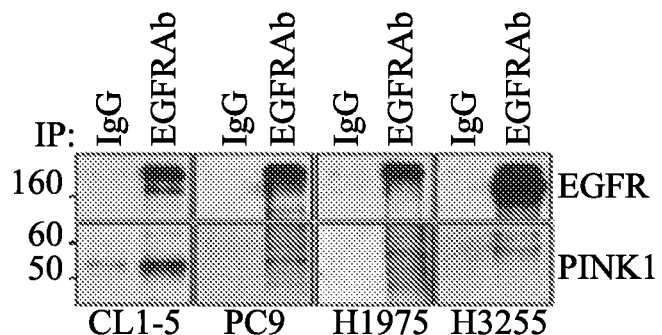
Figure 1C:
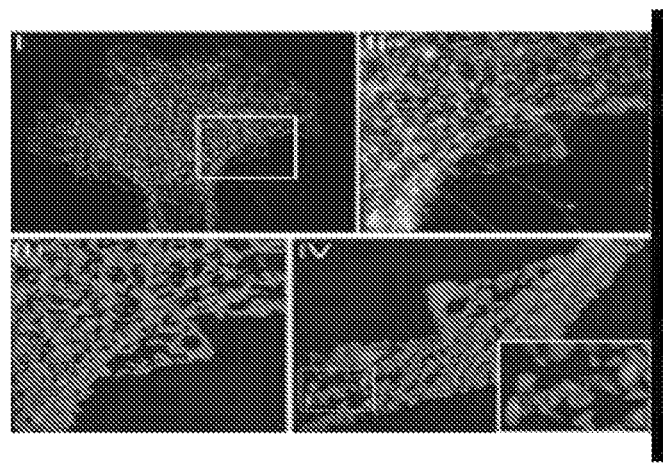

To determine whether PINK1 and EGFR interact in lung adenocarcinoma, endogenous PINK1 and EGFR were first examined in four lung adenocarcinoma cell lines bearing different types of EGFRs by immunoblotting: CL1-5 (wild-type), PC9 (Ex19Del), H1975 (L858R+T790M) and H3255 (L858R) (FIG. 1A). Total cell lysates were then immuno-precipitated with EGFR monoclonal antibody and immuno-blotted with PINK1 antibody. The results demonstrated the detection of PINK1 in the four immunoprecipitates, indicating the formation of endogenous protein complexes (FIG. 1B). To visualize the PINK1 and EGFR protein interaction, wild-type EGFR-GFP and PINK1-myc were co-overexpressed in CL1-5 cells. It is showed that these two proteins co-localized in CL1-5 cells and much of the co-localization occurred just beneath the cytoplasmic membrane (FIG. 1C). These data suggest a possible interaction between these two protein kinases regardless of EGFR mutational status.

Example 2 Inhibition of EGFR Dimerization and Internalization by PINK1

Since an interaction might exist between PINK1 and EGFR, the potential roles of PINK1 in EGFR were next investigated. PINK1 was knocked down in CL1-5, PC9, H1975 and H3255 cells, and it was found a decrease in total EGFR protein without simultaneous down-regulation of EGFR mRNA expression (FIGS. 2A, 2B and 2C). Decreased protein level without concurrent decline in mRNA expression suggests an augmented protein turnover. Based on current knowledge, EGFR turnover is mediated by receptor dimerization and internalization (A. V. Vieira, C. Lamaze, S. L. Schmid. *Science.* 274, 2086-2089 (1996); R. Heukers et al. *J. Cell. Sci.* 126, 4900-4912 (2013); and A. Tomas, C. E. Futter, E. R. *Trends. Cell. Biol.* 24, 26-34 (2014)). It was therefore studied whether PINK1 plays roles in these processes. To evaluate the alteration of EGFR dimerization under PINK1 manipulation, PINK1 knockdown cells and experimental-control cells were subjected to cell-based protein dimerization with BS3 after 6 h treatment with lysosome inhibitor (20 mM $NH_4Cl$) and proteasome inhibitor (10 μM MG132). For CL1-5 cells, EGF (50 ng/mL) was administered 20 minutes prior to cell harvest. Analyses by gradient SDS-PAGE and immunoblotting revealed an increase in the EGFR dimer to monomer ratio along with PINK1 knockdown. The pattern was observed among CL1-5, PC9, H1975 and H3255 cells bearing different types of EGFRs (FIG. 2D). To determine whether EGFR internalization is enhanced together with the increased dimer to monomer ratio, total cell lysates were fractionated into cell membranous and cytoplasmic fractions to check EGFR subcellular distribution. As demonstrated by CL1-5 and H1975 cells, the membranous fraction of EGFR was decreased and the cytoplasmic fraction of EGFR was increased under PINK1 knockdown, indicating an increase of receptor internalization (FIG. 2E). The data show that PINK1 knockdown facilitates EGFR dimerization and internalization, which lead to decreased total EGFR protein level.

Figure 7A:
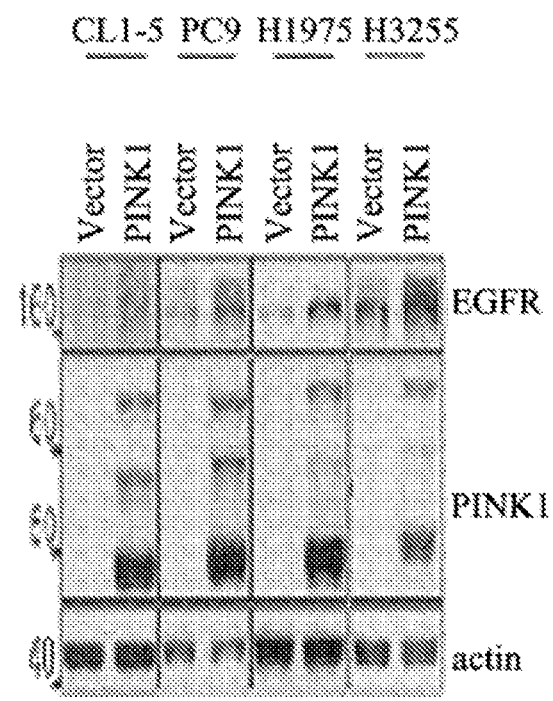
FIGS. 7A-7C show inhibition of EGFR dimerization by PINK1.
Figure 7B:
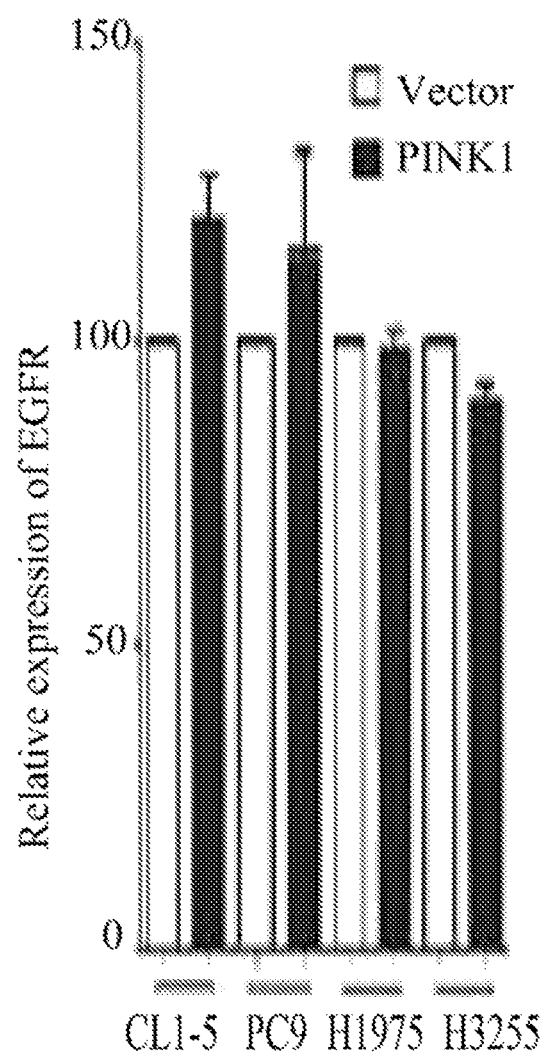
Figure 7C:
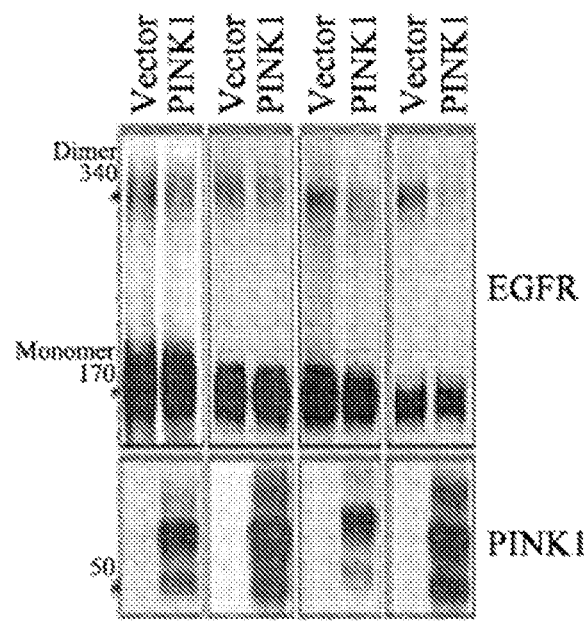

Next, PINK1 was overexpressed in CL1-5, PC9, H1975 and H3255 cells in order to clarify whether excess PINK1 proteins resulted in the opposite phenomenon. The results showed that total EGFR protein was increased without significant changes in EGFR mRNA expression (FIGS. 7A and 7B). In agreement, there was a decreased EGFR dimer to monomer ratio with PINK1 overexpression (FIG. 7C). Taken together, these data suggest that PINK1 affects the EGFR total protein level through its role in EGFR protein dimerization, internalization and turnover.

Example 3 Direct Interaction Between PINK1-CTD and EGFR-TKD

Figure 3A:
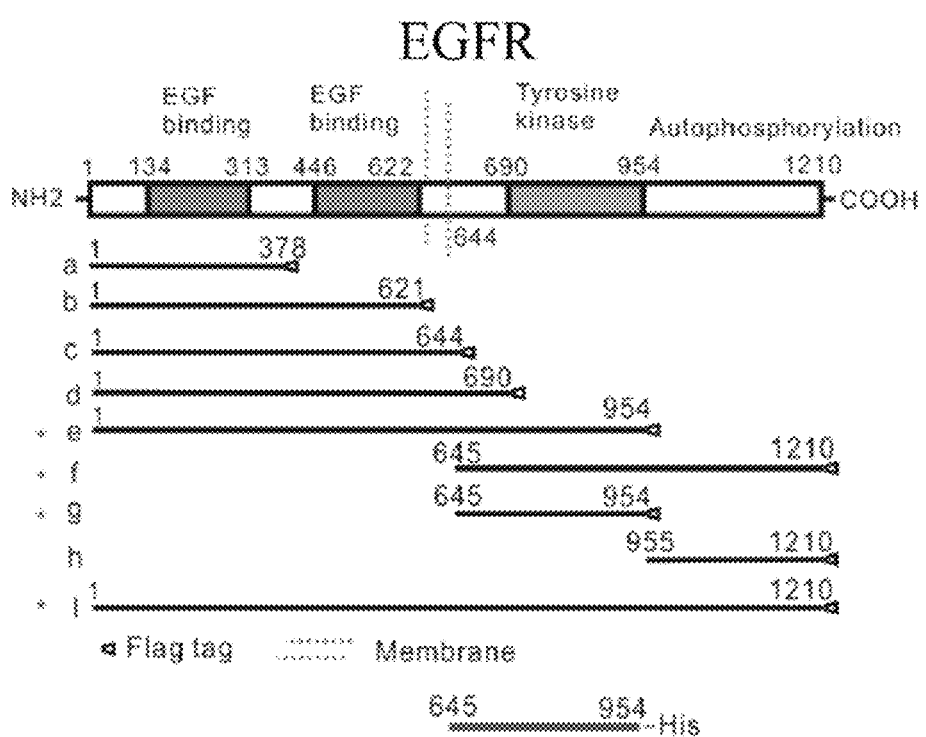
FIGS. 3A-3E show direct interaction between PINK1-CTD and EGFR-TKD.
Figure 3B:
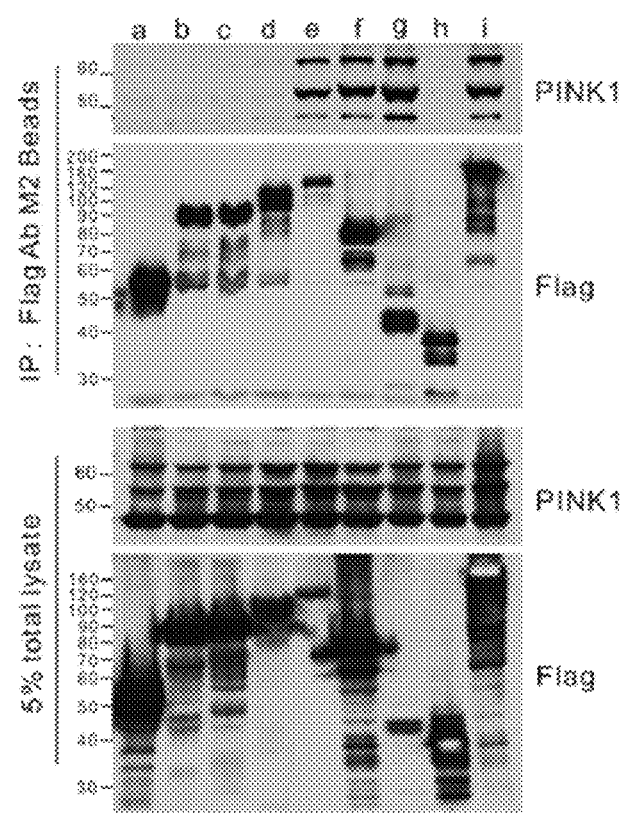
Figure 3C:
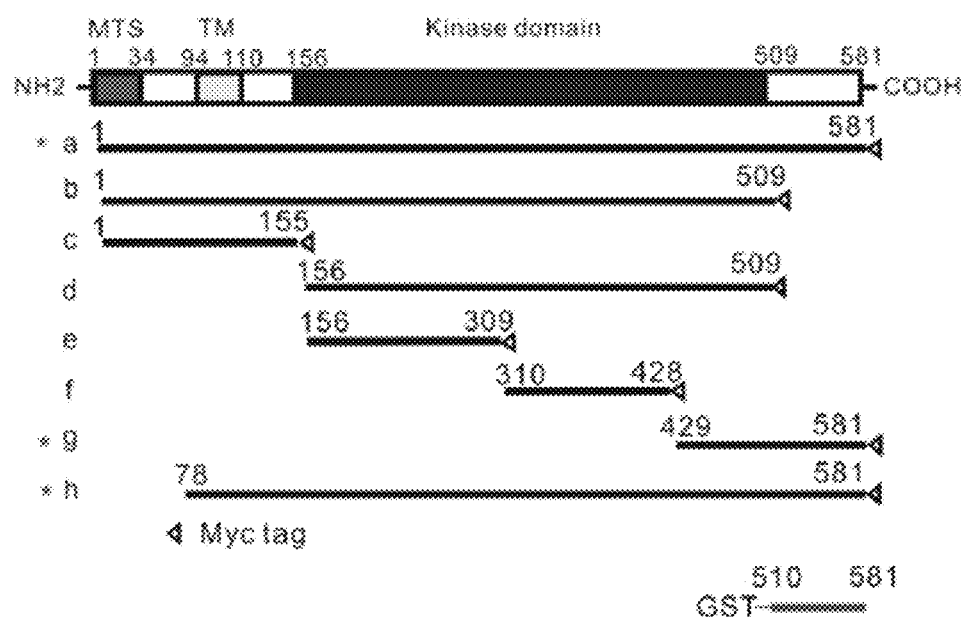
Figure 3D:
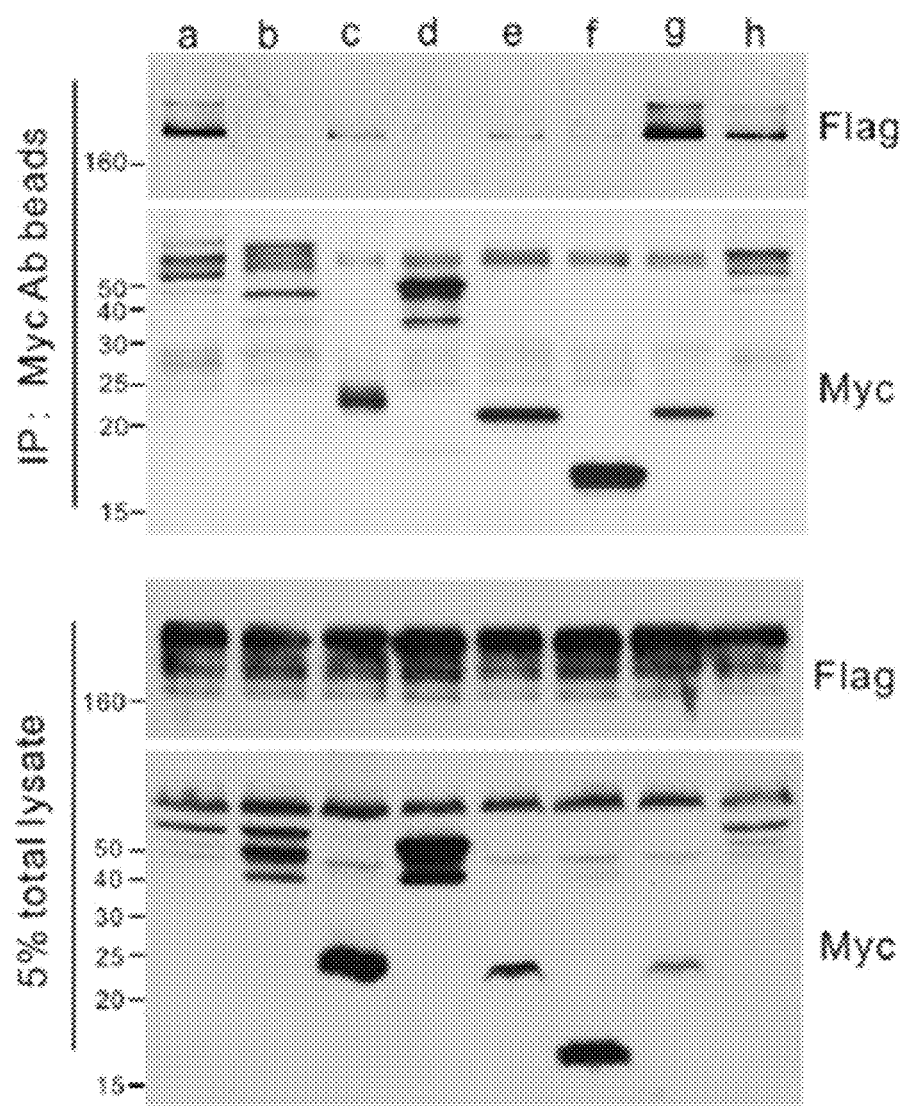
Figure 3E:
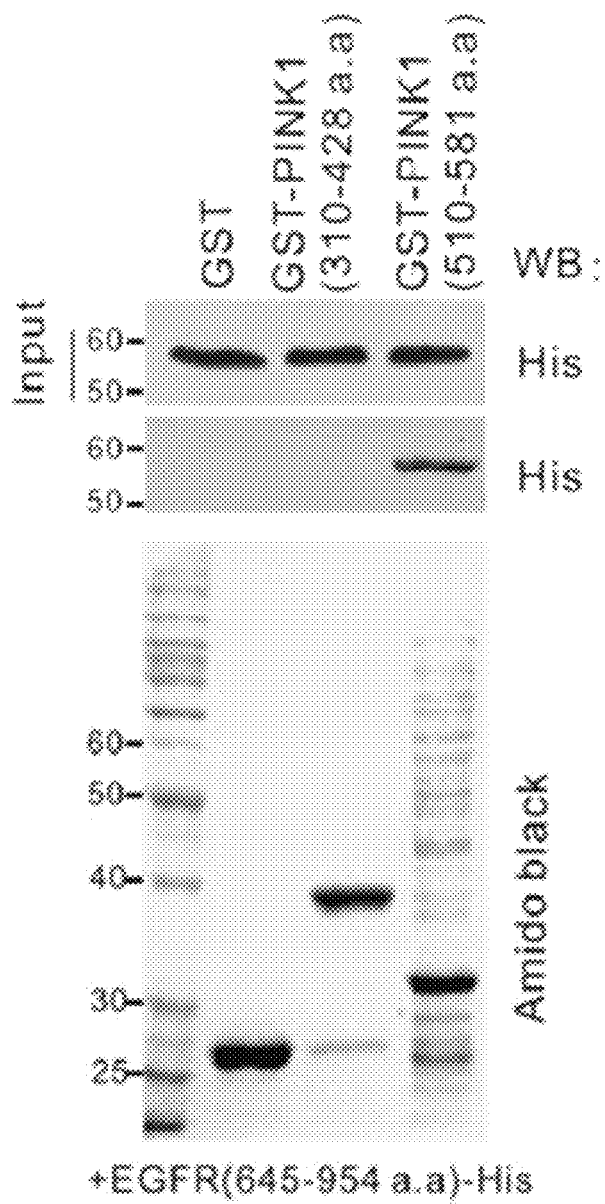

To dissect the interaction between PINK1 and EGFR, it was next investigated whether these two protein kinases interact directly and through which domains they interplay. It was established a flag-fused full-length EGFR construct, EGFR-flag, (amino acids 1-1210) and 8 serial truncated EGFR-flag constructs based on different EGFR functional domains (amino acids 1-378, 1-621, 1-644, 1-690, 1-954, 645-1210, 645-954, 955-1210) (FIG. 3A). Each of these 9 constructs was co-overexpressed with full-length PINK1 in HEK293 cells. The cell lysates were immunoprecipitated by anti-flag antibody and the immunoprecipitates were immunoblotted by PINK1 antibody. The data showed that only the full-length EGFR-flag construct and constructs that contained amino acids 1-954, 645-1210, and 655-954 interacted with PINK1, indicating that EGFR-TKD is an important region for PINK1 binding (FIG. 3B). It was simultaneously established a myc-fused full-length PINK1 construct and another 7 truncated PINK1-myc constructs containing amino acids 1-509, 1-155, 156-509, 156-309, 310-428, 429-581 and 78-581, respectively (FIG. 3C). Each of these 8 constructs was co-transfected with full-length EGFR-flag in HEK293 cells. The cell lysates were immunoprecipitated by anti-myc antibody and immunoblotted with anti-flag antibody. The data demonstrated that the amino acid 510-581 of PINK1 protein is the potential region that interacts with EGFR-TKD (FIG. 3D). To further confirm that direct interaction exists between EGFR-TKD and PINK1-CTD, it was performed in vitro the GST pull-down assay. Recombinant GST-fused PINK1-CTD (amino acids 510-581) and negative-control construct GST-fused PINK1310-428 (amino acids 310-428) were individually incubated with purified His-tagged EGFR-TKD (amino acids 645-954) and analyzed by immunoblotting with anti-His antibody (FIG. 3E). The results showed that PINK1-CTD directly bound to EGFR-TKD. These data demonstrate that PINK1 directly interacts with EGFR through PINK1-CTD and EGFR-TKD. This interaction plays a role in EGFR receptor dimerization, internalization and turnover.

Example 4 Inhibition of HER1 and HER2 Phosphorylation by PINK1-CTD

Figure 5A:
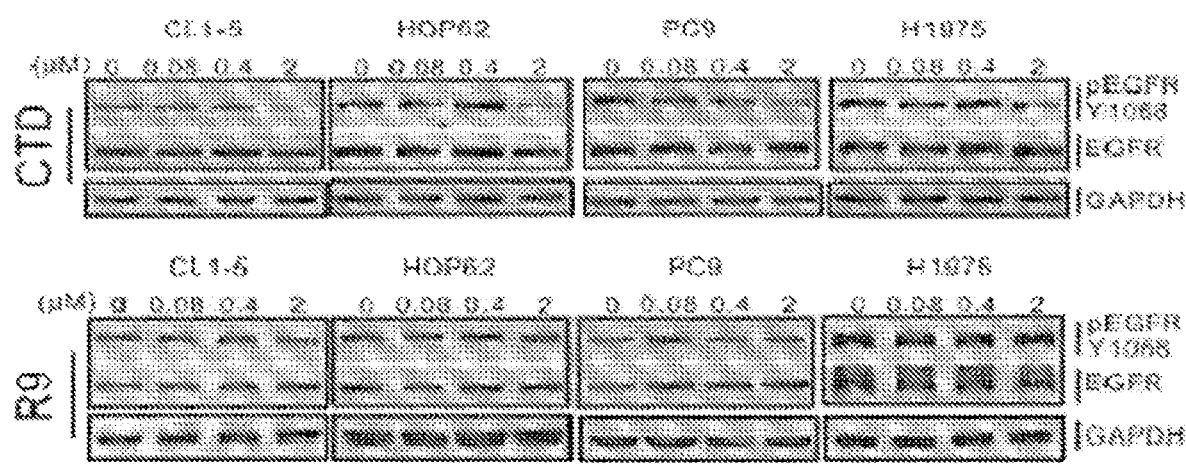
FIGS. 5A-5C show that PINK1-CTD inhibits HER1 (EGFR) and HER2 phosphorylation in lung cancer cells.
Figure 5B:
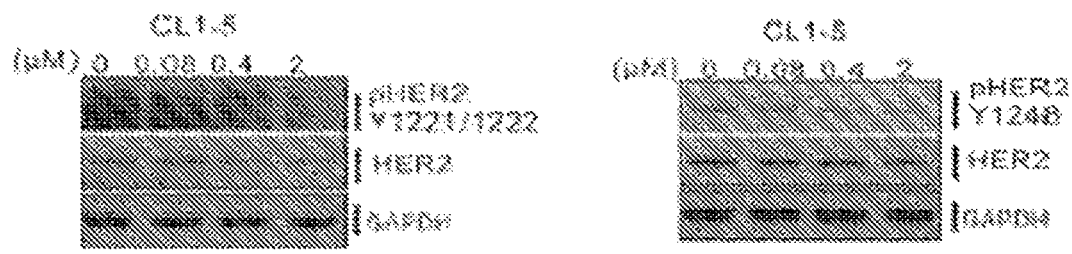
Figure 5C:
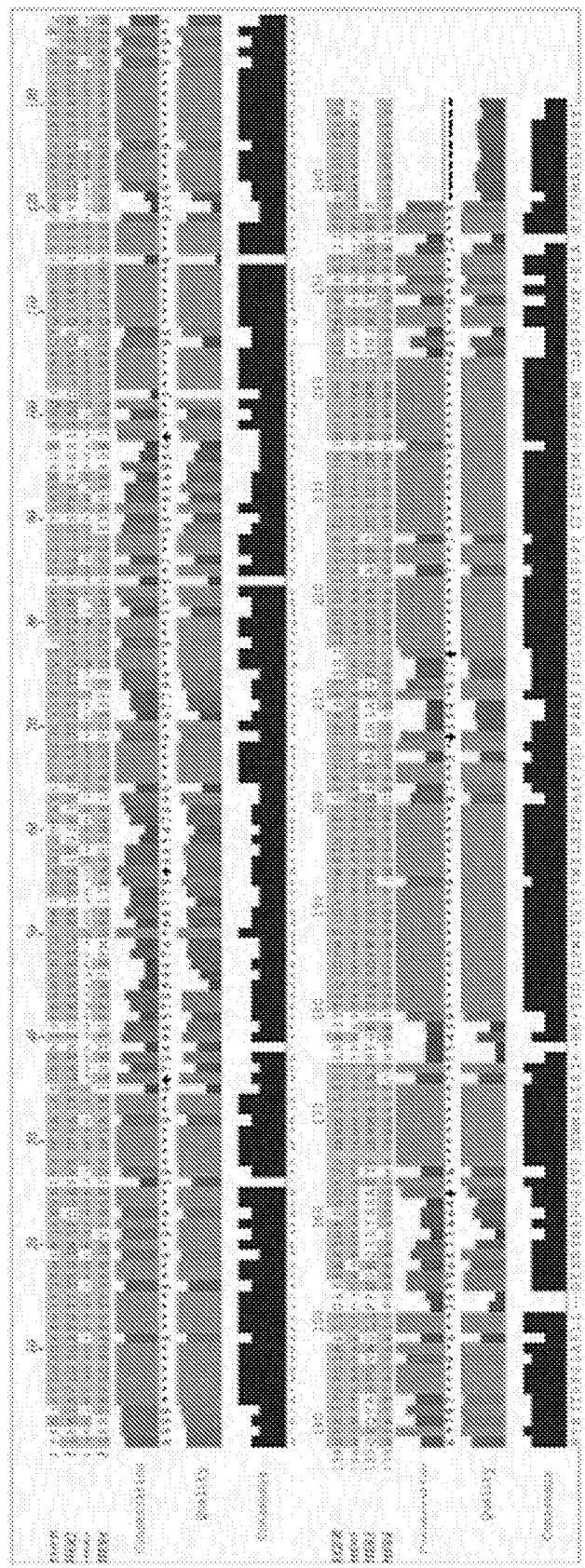

To determine the interaction between PINK1-CTD and HER1 or HER2, PINK1-CTD polypeptide was co-cultured with CL1-5, HOP62, PC9 or H1975 cells. In this example, the used PINK1-CTD was synthesized from Genmedkia Biotechnology Corp., and it was conjugated with 9 arginine residues for membrane attaching and internalization. The group in which the cells were co-cultured with a peptide only having 9 arginine residues (R9) was used as control group. The results showed that the CTD polypeptide effectively inhibited EGFR (HER1) phosphorylation in CL1-5, HOP62, PC9 and H1975 in cells (FIG. 5A). Also, CTD polypeptide inhibited HER2 phosphorylation in CL1-5 cell in a dose-dependent manner (FIG. 5B) Amino acid sequence alignment of the tyrosine kinase domain of ERBB1 to ERBB4 (HER1 to HER4) was performed, and the results showed that ERBB1 to ERBB4 revealed high sequence homology (FIG. 5C).

Figure 4:
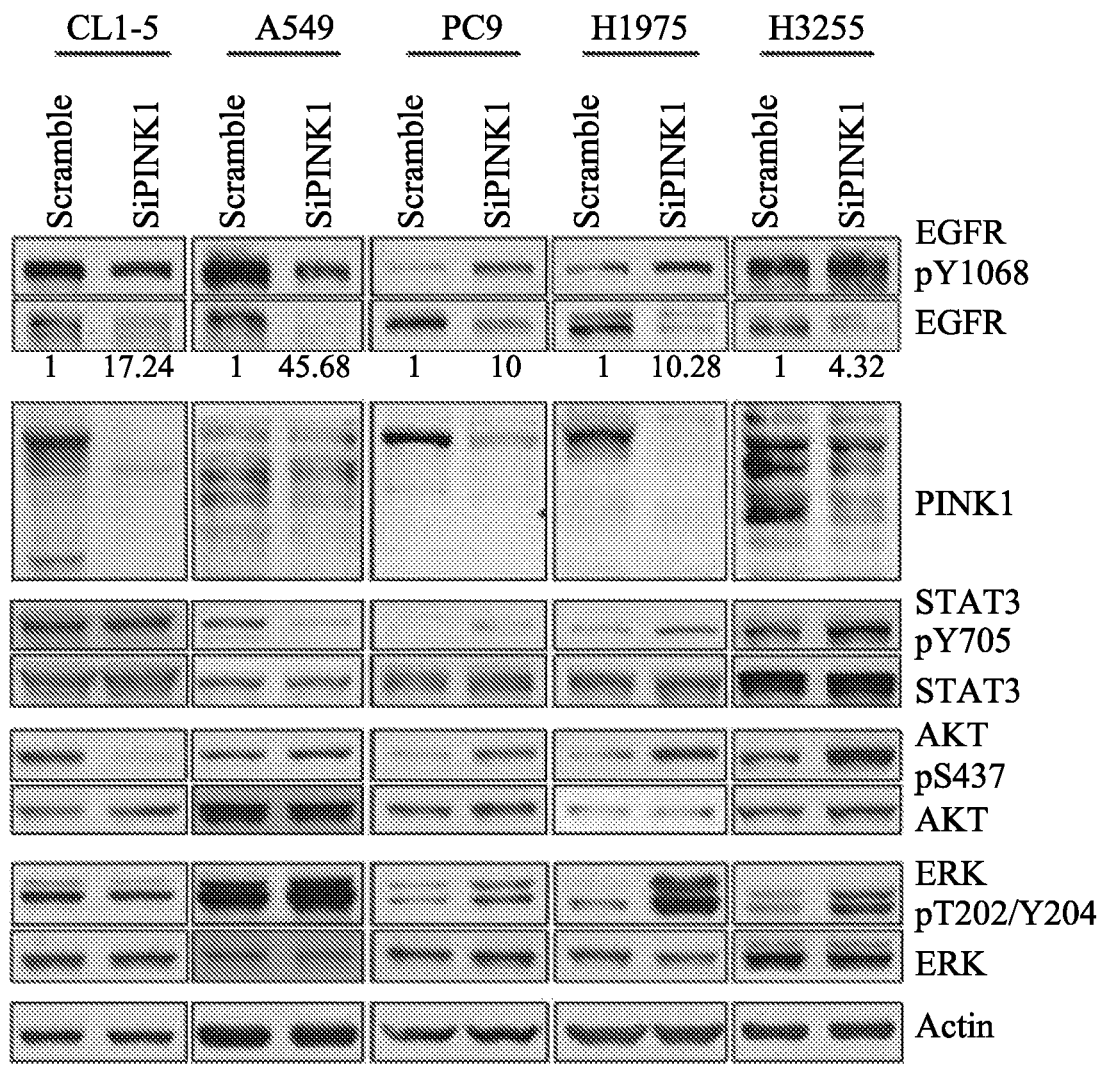
FIG. 4 shows impacts of PINK1 knockdown on EGFR pathway. Immunoblotting revealed enhanced EGFR-Y1068 phosphorylation under PINK1 knockdown in all tested cells. PINK1 knockdown intensified EGFR pathway activation in EGFR-addicted PC9, H1975 and H3255 cells but attenuated AKT-S473 phosphorylation in CL1-5 cells and STAT3-Y705 phosphorylation in A549 cells.
Figure 8:
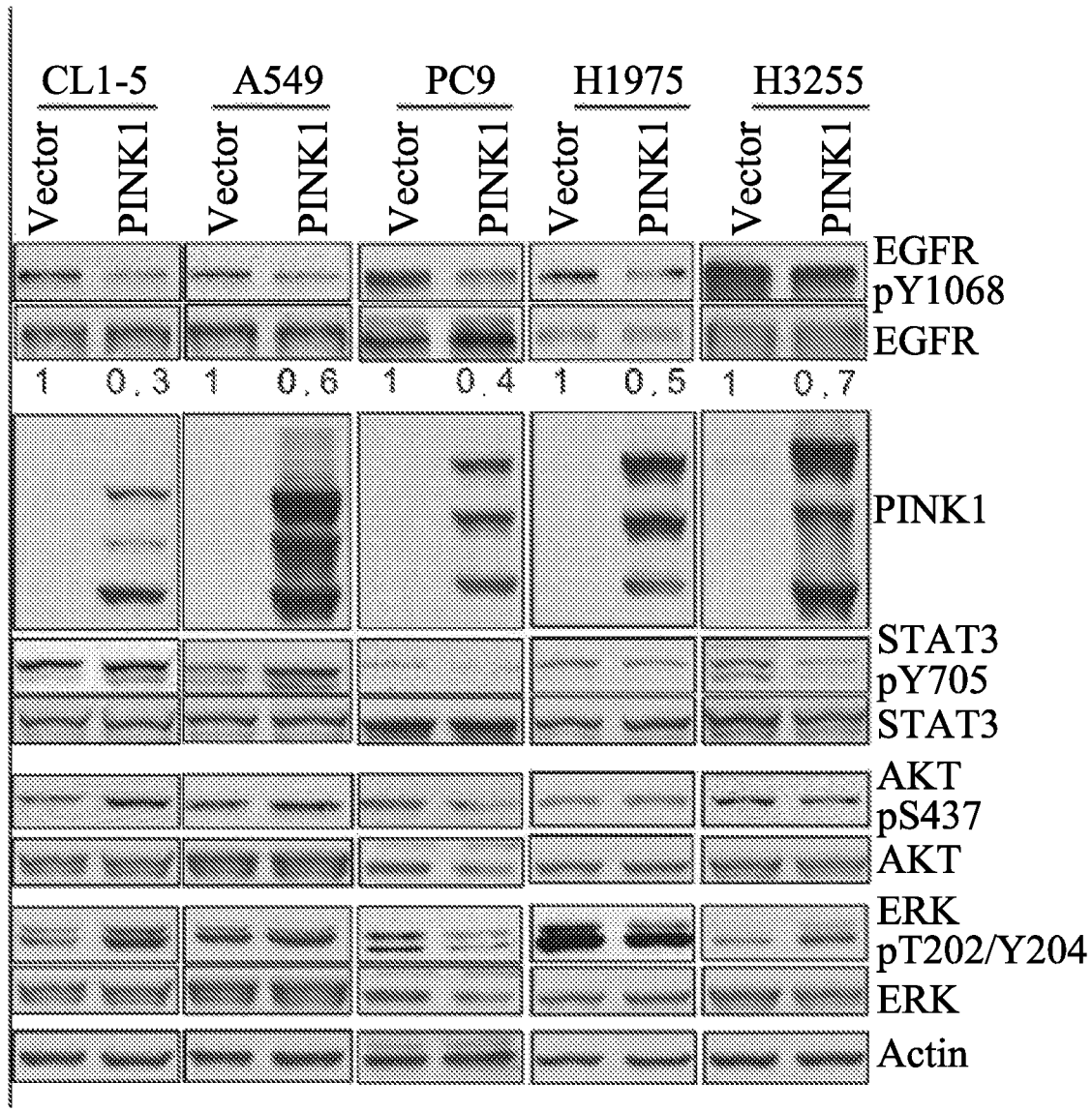
FIG. 8 shows impact of PINK1 overexpression on EGFR pathway. Immunoblotting demonstrated an attenuation of EGFR-Y1068 with PINK1 overexpression in all cells tested. PINK1 overexpression concurrently decreased the phosphorylation of STAT3-Y705, AKT-S473, or ERK-T202/Y204 in EGFR-addicted PC9 and H1975 cells. In H3255 cells, PINK1 overexpression attenuated STAT5-Y705 and AKT-S473 phosphorylation but enhanced ERK-T202/Y204 phosphorylation. In EGFR non-addicted CL1-5 and A549 cells, PINK1 overexpression increased the phosphorylation of STAT3-Y705, AKT-S473, or ERK-T202/Y204 even though EGFR-Y1068 phosphorylation was suppressed.
Figure 10:
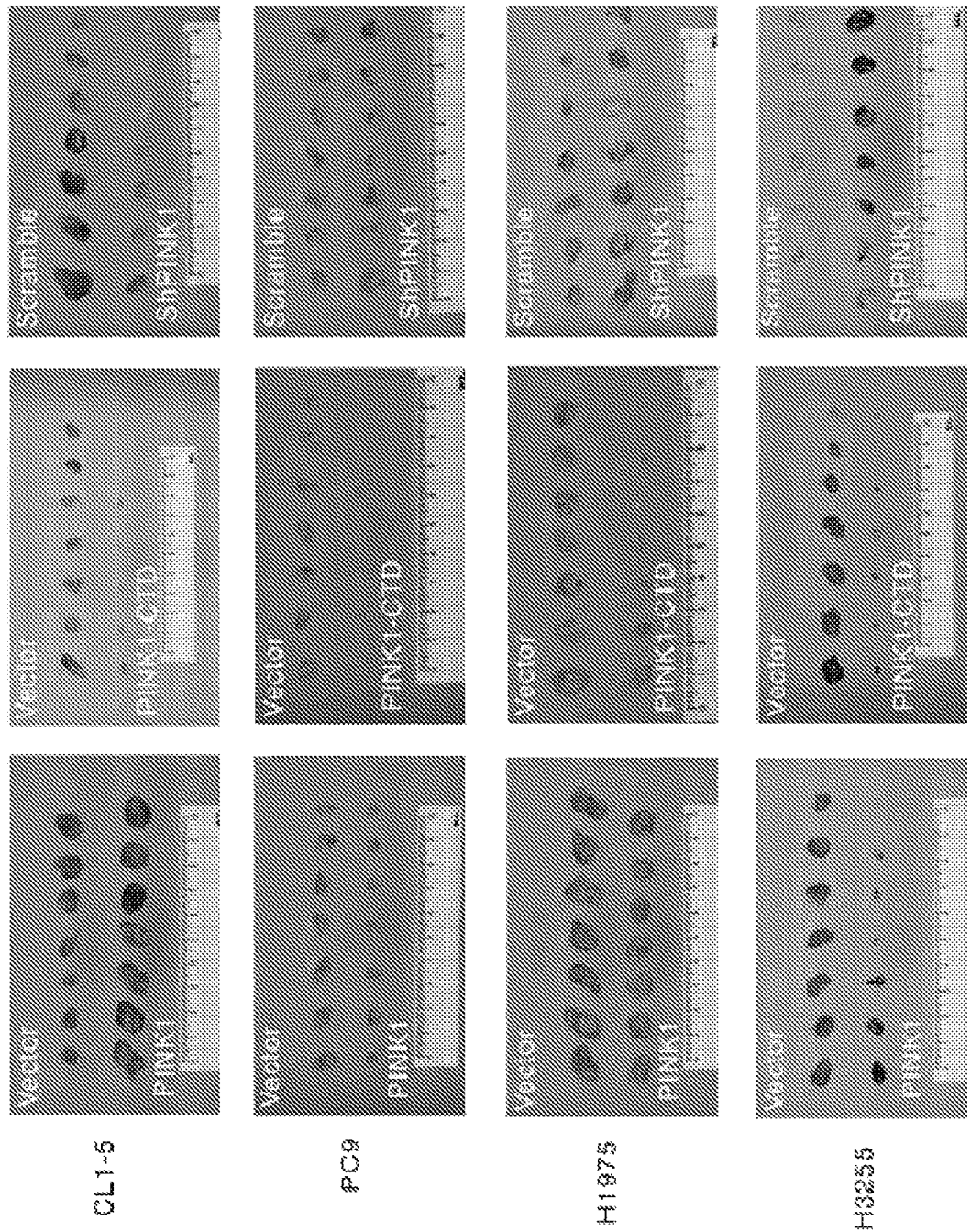
FIG. 10 shows gross pictures of tumor xenografts. PINK1 overexpression aggravated tumor growth in CL1-5 cells but suppressed tumor growth in PC9, H1975 and H3255 cells. PINK1-CTD overexpression inhibited tumor growth in all cells tested. PINK1 knockdown inhibited tumor growth in CL1-5 cells but promoted tumor growth in PC9 and H1975 cells. N=7 per each group.

Example 5 Aggravation of In Vivo Tumor Growth by PINK1 in EGFR Non-Addicted Cells Representative in vivo phenotypical alterations are particularly important in the study of molecular signaling. PINK1 knockdown was reported to reduce cell proliferation in several wild-type EGFR cell models (C. H. O'Flanagan, V. A. Morais, W. Wurst, B. De Strooper, C. O'Neill. Oncogene. (2014)). To examine whether such a phenomenon exists in wild-type EGFR lung adenocarcinoma cells, it was evaluated in vivo the tumor growth using shPINK1 and PINK1 stably expressing EGFR wild-type CL1-5 cells. The results showed that PINK1 knockdown retarded tumor growth while PINK1 overexpression aggravated tumor growth (FIGS. 6A and 6C, and FIG. 10). The observation is compatible with the immunoblotting results and is consistent with the general understanding that PINK1 functions as an oncogene in tumorigenesis (FIG. 4 and FIG. 8) (H. Murata et al. *J. Biol. Chem.* 286, 7182-7189 (2011); J. P. MacKeigan, L. O. Murphy, J. Blenis. *Nat. Cell. Biol.* 7, 591-600 (2005); S. A. Martin, M. Hewish, D. Sims, C. J. Lord, A. Ashworth. *Cancer. Res.* 71, 1836-1848 (2011); R. S. Akundi, L. Zhi, H. Büeler. *Neurobiol. Dis.* 45, 469-478 (2012); and C. H. O'Flanagan, V. A. Morais, W. Wurst, B. De Strooper, C. O'Neill. *Oncogene.* (2014)).

Example 6 Inhibition of In Vivo Tumor Growth by PINK1 in EGFR-Addicted Cells Although PINK1 promotes tumor growth in CL1-5 cells, the situation is the opposite in EGFR-addicted mutant cells, PC9, H1975 and H3255. ShPINK1 and PINK1 stably expressing cells were used in tumor xenograft experiments. The results showed that PINK1 knockdown sped up tumor growth, which was consistent with the enhanced EGFR pathway activation shown by immunoblotting (FIGS. 6F, 6I and 6L, FIG. 4, and FIG. 10). In contrast, PINK1 overexpression appeared to retard tumor growth, including the EGFR T790M mutant expressing H1975 xenografts (FIGS. 6D, 6G and 6J, FIG. 8 and FIG. 10). In this context, PINK1 serves as a tumor suppressor, the role originally suggested when it was first identified but never verified (M. Unoki, Y. Nakamura. *Oncogene.* 22, 2172-2185 (2003)). Collectively, these data suggest that the discrepancies observed among different cell types can be attributed to EGFR addiction or non-addiction.

Figure 9A:
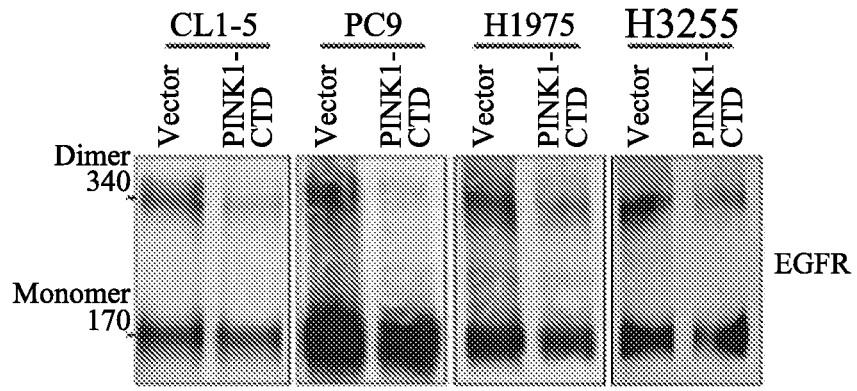
FIGS. 9A and 9B show hindrance of PINK1-CTD to EGFR dimerization and activation.
Figure 9B:
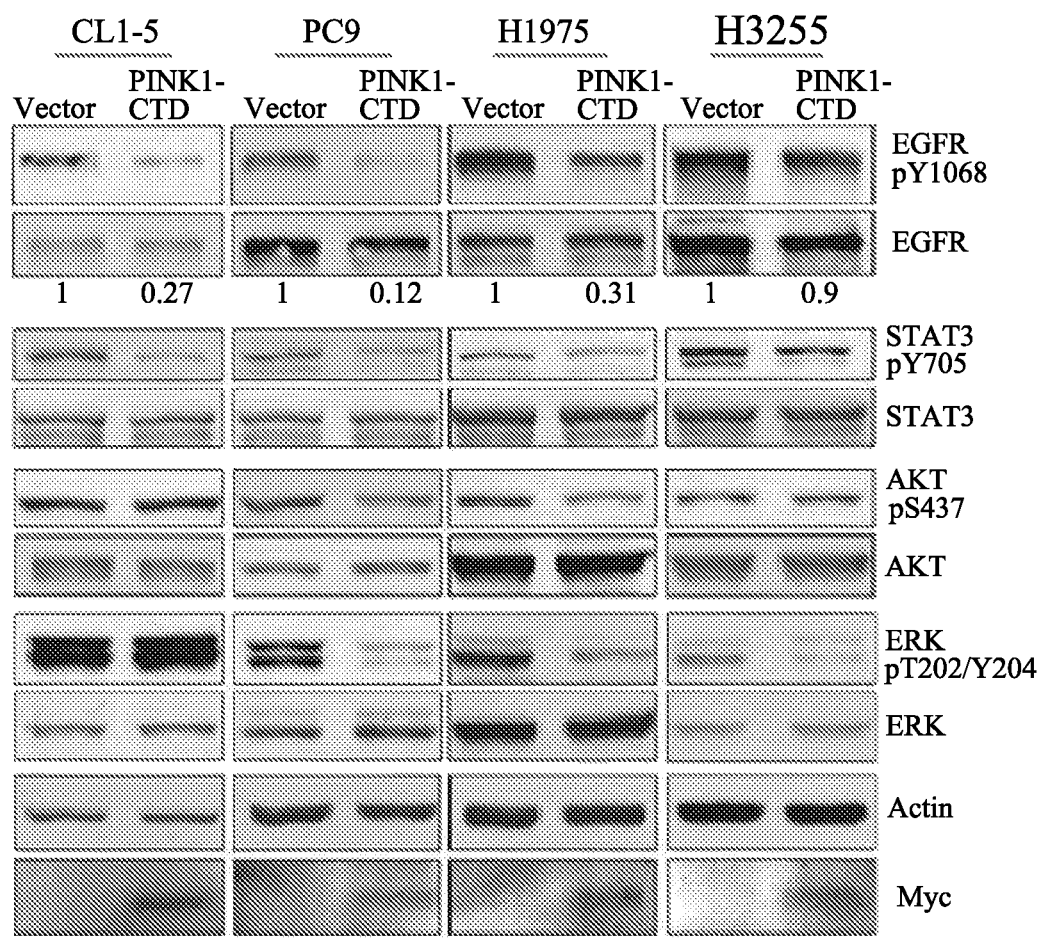

Example 7 Anti-Tumor Effect of PINK1-CTD on Both EGFR-Addicted and EGFR Non-Addicted Cells It was next investigated the in vivo tumor growth of PINK1-CTD stably expressing CL1-5, PC9, H1975 and H3255 cells. It has been shown that PINK1-CTD inhibits EGFR activation. It not only downregulates EGFR downstream signaling in EGFR-addicted PC9, H1975 and H3255 cells but also attenuates STAT5-Y705 phosphorylation in EGFR non-addicted CL1-5 cells (FIGS. 9A and 9B). Consistent with the immunoblotting results, in vivo tumor xenografts proved that PINK1-CTD exerted inhibitory effects in all the cells tested (FIGS. 6B, 6E, 6H, and 6K). In addition, the synthetic polypeptide PINK1-CTD (Genmedkia Biotechnology Corp.) was used in mouse xenograft model. 2 µM of CTD polypeptide or R9 peptide (as control group) was injected into the mouse every day or every two days (as shown by arrow in FIGS. 11A and 11B). The results showed that PINK1-CTD treatment inhibited in vivo tumor growth in CL1-5 and H1975 lung cancer mouse xenograft models (FIGS. 11A and 11B). This observation is compatible with the results of in vitro MTT assay, which showed that the viabilities of CL1-5, H1975, PC9 and Hop62 were reduced by 2 µM of CTD polypeptide (FIG. 11C).

These results strengthen the supposition that the oncogenic function of PINK1 resides in regions outside its C-terminal domain, and the tumor-inhibitory effect of PINK1-CTD relies on cells' dependency on EGFR signaling. Even though CL1-5 is EGFR non-addicted, the observed tumor retardation effect of PINK1-CTD suggests the importance of aberrant EGFR-STATS signaling in CL1-5 cells. The results, therefore, point to the therapeutic potential of PINK1-CTD in lung adenocarcinoma.

---

What is claimed is:

1. A non-natural polypeptide binding to ERBB tyrosine kinase domain (ERBB-TKD), or a biologically active variant thereof, wherein the non-natural polypeptide or the biologically active variant thereof consists of SEQ ID NO:1.

2. The non-natural polypeptide of claim 1, wherein the ERBB is ERBB1, ERBB2, ERBB3 or ERBB4.

3. The non-natural polypeptide of claim 1, wherein the ERBB-TKD is EGFR-TKD.

4. A pharmaceutical composition comprising a therapeutically effective amount of the non-natural polypeptide of claim 1, and a pharmaceutically acceptable carrier thereof.

5. The pharmaceutical composition of claim 4, further comprising an additional anti-cancer agent.

6. The pharmaceutical composition of claim 5, wherein the additional anti-cancer agent is an ERBB inhibitor or an EGFR inhibitor.

7. The pharmaceutical composition of claim 6, wherein the EGFR inhibitor is selected from the group consisting of gefitinib, erlotinib, cetuximab, afatinib, necitumumab, nimotuzumab, PF299804, RO5083945, ABT-806, NVP-TAE684 and a combination thereof.

* * * * *

SEQUENCE LISTING

```
<160> NUMBER OF SEQ ID NOS: 2

<210> SEQ ID NO 1
<211> LENGTH: 72
<212> TYPE: PRT
<213> ORGANISM: Homo sapiens

<400> SEQUENCE: 1

Ser Leu Trp Gly Glu His Ile Leu Ala Leu Lys Asn Leu Lys Leu Asp
1               5                   10                  15

Lys Met Val Gly Trp Leu Leu Gln Gln Ser Ala Ala Thr Leu Leu Ala
                20                  25                  30

Asn Arg Leu Thr Glu Lys Cys Cys Val Glu Thr Lys Met Lys Met Leu
            35                  40                  45

Phe Leu Ala Asn Leu Glu Cys Glu Thr Leu Cys Gln Ala Ala Leu Leu
        50                  55                  60

Leu Cys Ser Trp Arg Ala Ala Leu
65                  70

<210> SEQ ID NO 2
<211> LENGTH: 581
<212> TYPE: PRT
<213> ORGANISM: Homo sapiens

<400> SEQUENCE: 2

Met Ala Val Arg Gln Ala Leu Gly Arg Gly Leu Gln Leu Gly Arg Ala
1               5                   10                  15

Leu Leu Leu Arg Phe Thr Gly Lys Pro Gly Arg Ala Tyr Gly Leu Gly
                20                  25                  30

Arg Pro Gly Pro Ala Ala Gly Cys Val Arg Gly Glu Arg Pro Gly Trp
            35                  40                  45

Ala Ala Gly Pro Gly Ala Glu Pro Arg Arg Val Gly Leu Gly Leu Pro
        50                  55                  60

Asn Arg Leu Arg Phe Phe Arg Gln Ser Val Ala Gly Leu Ala Ala Arg
65                  70                  75                  80

Leu Gln Arg Gln Phe Val Val Arg Ala Trp Gly Cys Ala Gly Pro Cys
                85                  90                  95

Gly Arg Ala Val Phe Leu Ala Phe Gly Leu Gly Leu Gly Leu Ile Glu
            100                 105                 110

Glu Lys Gln Ala Glu Ser Arg Arg Ala Val Ser Ala Cys Gln Glu Ile
        115                 120                 125

Gln Ala Ile Phe Thr Gln Lys Ser Lys Pro Gly Pro Asp Pro Leu Asp
    130                 135                 140

Thr Arg Arg Leu Gln Gly Phe Arg Leu Glu Glu Tyr Leu Ile Gly Gln
145                 150                 155                 160
```

-continued

Ser Ile Gly Lys Gly Cys Ser Ala Ala Val Tyr Glu Ala Thr Met Pro
              165                 170                 175

Thr Leu Pro Gln Asn Leu Glu Val Thr Lys Ser Thr Gly Leu Leu Pro
              180                 185                 190

Gly Arg Gly Pro Gly Thr Ser Ala Pro Gly Glu Gly Gln Glu Arg Ala
              195                 200                 205

Pro Gly Ala Pro Ala Phe Pro Leu Ala Ile Lys Met Met Trp Asn Ile
              210                 215                 220

Ser Ala Gly Ser Ser Ser Glu Ala Ile Leu Asn Thr Met Ser Gln Glu
225                 230                 235                 240

Leu Val Pro Ala Ser Arg Val Ala Leu Ala Gly Glu Tyr Gly Ala Val
              245                 250                 255

Thr Tyr Arg Lys Ser Lys Arg Gly Pro Lys Gln Leu Ala Pro His Pro
              260                 265                 270

Asn Ile Ile Arg Val Leu Arg Ala Phe Thr Ser Ser Val Pro Leu Leu
              275                 280                 285

Pro Gly Ala Leu Val Asp Tyr Pro Asp Val Leu Pro Ser Arg Leu His
              290                 295                 300

Pro Glu Gly Leu Gly His Gly Arg Thr Leu Phe Leu Val Met Lys Asn
305                 310                 315                 320

Tyr Pro Cys Thr Leu Arg Gln Tyr Leu Cys Val Asn Thr Pro Ser Pro
              325                 330                 335

Arg Leu Ala Ala Met Met Leu Leu Gln Leu Leu Glu Gly Val Asp His
              340                 345                 350

Leu Val Gln Gln Gly Ile Ala His Arg Asp Leu Lys Ser Asp Asn Ile
              355                 360                 365

Leu Val Glu Leu Asp Pro Asp Gly Cys Pro Trp Leu Val Ile Ala Asp
              370                 375                 380

Phe Gly Cys Cys Leu Ala Asp Glu Ser Ile Gly Leu Gln Leu Pro Phe
385                 390                 395                 400

Ser Ser Trp Tyr Val Asp Arg Gly Gly Asn Gly Cys Leu Met Ala Pro
              405                 410                 415

Glu Val Ser Thr Ala Arg Pro Gly Pro Arg Ala Val Ile Asp Tyr Ser
              420                 425                 430

Lys Ala Asp Ala Trp Ala Val Gly Ala Ile Ala Tyr Glu Ile Phe Gly
              435                 440                 445

Leu Val Asn Pro Phe Tyr Gly Gln Gly Lys Ala His Leu Glu Ser Arg
              450                 455                 460

Ser Tyr Gln Glu Ala Gln Leu Pro Ala Leu Pro Glu Ser Val Pro Pro
465                 470                 475                 480

Asp Val Arg Gln Leu Val Arg Ala Leu Leu Gln Arg Glu Ala Ser Lys
              485                 490                 495

Arg Pro Ser Ala Arg Val Ala Ala Asn Val Leu His Leu Ser Leu Trp
              500                 505                 510

Gly Glu His Ile Leu Ala Leu Lys Asn Leu Lys Leu Asp Lys Met Val
              515                 520                 525

Gly Trp Leu Leu Gln Gln Ser Ala Ala Thr Leu Leu Ala Asn Arg Leu
              530                 535                 540

```
-continued

Thr Glu Lys Cys Cys Val Glu Thr Lys Met Lys Met Leu Phe Leu Ala
545                 550                 555                 560

Asn Leu Glu Cys Glu Thr Leu Cys Gln Ala Ala Leu Leu Leu Cys Ser
                565                 570                 575

Trp Arg Ala Ala Leu
                580
```